United States Patent [19]

Cooper et al.

[11] Patent Number: 5,260,275
[45] Date of Patent: Nov. 9, 1993

[54] HYPOGLYCEMICS

[75] Inventors: Garth J. S. Cooper, Solana Beach; Candace X. Moore, San Diego, both of Calif.

[73] Assignee: Amylin Pharmaceuticals, Inc., San Diego, Calif.

[21] Appl. No.: 567,919

[22] Filed: Aug. 14, 1990

[51] Int. Cl.[5] .................. A61K 37/02; A61K 37/43
[52] U.S. Cl. ............................. 514/12; 514/13; 514/866
[58] Field of Search ............... 514/12, 21, 808, 866, 514/884, 13; 424/85.8; 530/307, 324

[56] References Cited

FOREIGN PATENT DOCUMENTS 309100 3/1989 European Pat. Off. .
89/06135 7/1989 World Int. Prop. O. .

OTHER PUBLICATIONS

Leighton et al, "Pancreatic amylin and CGRP cause resistance to insulin . . . ", *Nature* 335:632-35 (1988).
Mitsukawa et al, "Islet Amyloid Polypeptide Response to Glucose, Insulin, . . . ", *Diabetes*, vol. 39, May 1990, pp. 639-642.
Moline et al, "Induction of Insulin Resistance In Vivo by Amylin and CRP", *Diabetes*, vol. 39, Feb. 1990, pp. 260-265.
Westermark et al., *Proc. Natl. Acad. Sci. U.S.A.* 84:3881-85 (1987).
Cooper et al., *Proc. Natl. Acad. Sci. U.S.A.* 84:8628-32 (1987).
*Joslin's Diabetes Mellitus*, Chapter 21 (12th ed. 1985).
*Goodman and Gilman's: The Pharmacological Basis of Therapeutics*, p. 1504 (7th ed. 1988).
Nishi et al., *Journal of Biological Chemistry* 265:4173-76 (1990).
Clark, *Diab. Med.* 6:561-67 (1989).
Cooper et al., *Biochim. Biophy. Acta* 1014:247-58 (1989).
Cooper et al., *Diabetes* 1988, pp. 493-496, Larkins, Zimmet, and Chisholm (Eds.), (Elsevier Science Publishers B. V. 1989).
Cooper et al., *Progress in Growth Factor Research* 1:99-105 (1989);
Johnson et al., *New England Journal of Medicine* 321:513-18 (1989).

*Primary Examiner*—Jeffrey E. Russel
*Attorney, Agent, or Firm*—Lyon & Lyon

[57] ABSTRACT

Non-insulin dependent, or type 2, diabetes mellitus in a patient is treated by administering to the patient a hypoglycemic agent that enhances plasma concentrations of amylin and a therapeutically effective amount of an amylin antagonist. Hypoglycemic agents which enhance plasma concentrations of amylin can be sulfonylureas such as glibenclamide and tolbutamide. Amylin antagonists can be amylin 8-37 and CGRP 8-37. Administration of the amylin antagonist in conjunction with the hypoglycemic agent also enhances the blood glucose lowering effects of the hypoglycemic agent.

13 Claims, 6 Drawing Sheets

* SIGNIFICANTLY DIFFERENT FROM CONTROLS (ABSENCE OF HYPOGLYCEMIC AGENT); P<0.02

* SIGNIFICANTLY DIFFERENT FROM CONTROLS (ABSENCE OF HYPOGLYCEMIC AGENT); P<0.02

* SIGNIFICANTLY DIFFERENT FROM CONTROLS (ABSENCE OF HYPOGLYCEMIC AGENT); P<0.02

* SIGNIFICANTLY DIFFERENT FROM CONTROLS (ABSENCE OF HYPOGLYCEMIC AGENT); P<0.02

HYPOGLYCEMICS

BACKGROUND

1. Field of the Invention

The field of the invention is medicine and, more particularly, methods, compounds and compositions for the treatment of non-insulin-dependent, or Type 2, diabetes mellitus.

2. Description of Related Art and Introduction to the Invention

Diabetes mellitus is the most common of the serious metabolic diseases affecting humans. It may be defined as a state of chronic hyperglycemia, i.e., excess sugar in the blood, consequent upon a relative or absolute lack of insulin action. Insulin is a peptide hormone produced and secreted by B cells within the islets of Langerhans in the pancreas. Insulin promotes glucose utilization, protein synthesis, and the formation and storage of neutral lipids. It is generally required for the entry of glucose into muscle. Glucose, or "blood sugar", is normally present in humans at concentrations of about 0.8-1.2 grams (4.0-7.0 millimoles) per liter and is the principal source of carbohydrate energy for man and many other organisms. Excess glucose is stored in the body (especially in the liver and muscles) as glycogen, a starch-like substance which is, essentially, polymerized glucose. Glycogen is metabolized into glucose as needed to meet bodily requirements.

Glucose normally stimulates both the secretion and biosynthesis of insulin. In addition to this glucose-stimulated insulin secretion, however, there exists a basal insulin secretion, the biological process by which insulin is released into the circulation in the absence of stimulation by levels of glucose, or other agents that promote insulin secretion, that are elevated above their "fasting" or non-fed levels. The normal basal (or fasting) level of insulin is usually about 10–16 KU/ml (or 440–700 pmol/L) which occurs during normal fasting glucose levels of about 4.0 to 5.5 mmol/L. Levels of insulin secretion stimulated by glucose amounts elevated above the normal fasting level of glucose can reach or exceed 320 µU/ml (or 14 nmol/L) in nondiabetics.

Glycogen is normally synthesized from glucose at a basal rate, i.e., the rate of synthesis that proceeds in the absence of glucose-stimulated insulin secretion. At the normal basal rate of insulin secretion, in fact, about 90 percent of total glycogen synthesis is probably not directly stimulated by insulin. Of course, insulin-stimulated glycogen synthesis is a normal occurrence and, at the maximal glucose-stimulated insulin secretion rate, approximately seventy percent of total glycogen synthesis is caused by direct insulin stimulation.

The hyperglycemia associated with diabetes mellitus is a consequence of both the underutilization of glucose and the overproduction of glucose from protein due to relatively depressed or nonexistent levels of insulin. In so-called Type 2 diabetics, for example, maximally glucose-stimulated insulin levels typically fail to rise above 90 µU/ml (4.0 nmol/L).

Not only is diabetes mellitus characterized by a series of hormone induced metabolic abnormalities, but also by long term complications involving the eyes, nerves, kidneys and blood vessels, and by a lesion involving thickening of the cellular basement membranes. These diabetic complications include premature atherosclerosis, intercapillary glomerulosclerosis, retinopathy, and neuropathy. The major cause of death and disability in diabetes is coronary artery disease. Garcia McNamara P. M., Gordon T., Kannell W. E., *Morbidity and Mortality in Diabetics in the Framingham Population. Sixteen Year Follow-up.* Diabetes 1974; 34:105-111. This publication and all other references noted herein are hereby incorporated by reference.

Although the diagnosis of symptomatic diabetes mellitus is not difficult, detection of asymptomatic disease can raise a number of problems. Diagnosis may usually be confirmed by the demonstration of fasting hyperglycemia. In borderline cases, the well-known glucose tolerance test is usually applied. Some evidence suggests, however, that the oral glucose tolerance test over-diagnoses diabetes to a considerable degree, probably because stress from a variety of sources (mediated through the release of the hormone epinephrine) can cause an abnormal response. In order to clarify these difficulties, the National Diabetes Data Group of the National Institutes of Health have recommended criteria for the diagnosis of diabetes following a challenge with oral glucose. National Diabetes Data Group: *Classification and Diagnosis of Diabetes Mellitus and Other Categories of Glucose Intolerance.* Diabetes 1979; 28:1039.

The frequency of diabetes mellitus in the general population is difficult to ascertain with certainty, but the disorder is believed to affect more than ten million Americans. Diabetes mellitus generally cannot be cured but only controlled. In recent years it has become apparent that there are a series of different syndromes included under the umbrella term "diabetes mellitus". These syndromes differ both in clinical manifestations and in their pattern of inheritance. The term diabetes mellitus is considered to apply to a series of hyperglycemic states which exhibit the characteristics noted above.

Diabetes mellitus has been classified into two basic categories, primary and secondary, and includes impaired glucose tolerance, which may be defined as a state associated with abnormally elevated blood glucose levels after an oral glucose load, in which the degree of elevation is insufficient to allow a diagnosis of diabetes to be made. Persons in this category are at increased risk for the development of fasting hyperglycemia or symptomatic diabetes relative to persons with normal glucose tolerance, although such a progression cannot be predicted in individual patients. In fact, several large studies suggest that most patients with impaired glucose tolerance (approximately 75 percent) never develop diabetes. See Jarrett A.l., Keen H., Fuller J. H., Mccartney M., *Worsening to Diabetes in Men with Impaired Glucose Tolerance ("Borderline diabetes").* Diabetologia 1979; 16:25-30.

Primary diabetes mellitus includes:
1. Insulin-dependent diabetes mellitus (IDDM, or Type I)
2. Non-insulin-dependent diabetes mellitus (NIDDM, or Type 2)
   a. Non-obese Type 2
   b. Obese Type 2
   c. Maturity-onset diabetes of the young (MODY).

Secondary diabetes mellitus includes diabetes mellitus secondary to:
1. Pancreatic disease 2. Hormonal abnormalities other than primary lack of insulin action (e.g., Cushings disease, Acromegaly, Phaeochromacytoma)
3. Drug or chemical induction
4. Insulin receptor abnormalities
5. Genetic syndromes
6. Other.

It should be noted that the category of secondary diabetes mellitus is of markedly less importance than is that of primary diabetes mellitus in terms of the absolute numbers of individuals affected, at least in the western world. Also, the appearance of abnormal carbohydrate metabolism in association with any of the above secondary causes does not necessarily indicate the presence of underlying diabetes although in many cases a mild asymptomatic, primary diabetes may be made overt by the secondary illness.

Type 2 or non-insulin-dependent diabetes is of present concern herein. Insulin resistance is a characteristic of Type 2 diabetes and may be defined as a failure of the normal metabolic response of peripheral tissues to the action of insulin. In other words, it is a condition where the presence of insulin produces a subnormal biological response. In clinical terms, insulin resistance is present when normal or elevated blood glucose levels persist in the face of normal or elevated levels of insulin. It represents, in essence, a glycogen synthesis inhibition, by which either basal or insulin-stimulated glycogen synthesis, or both, are reduced below normal levels. Insulin resistance plays a major role in Type 2, as demonstrated by the fact that the hyperglycemia present in Type 2 diabetes can sometimes be reversed by diet or weight loss sufficient, apparently, to restore the sensitivity of peripheral tissues to insulin. There are at least two causes of hyperglycemia in Type 2 diabetes.

1. Failure of glucose storage to be activated—It is known that the storage of carbohydrate as glycogen is a likely consequence of intermittent carbohydrate feeding because each calorie load can easily exceed immediate metabolic needs. In the short term, storage provides a means of clearing the plasma of glucose. Recent data have suggested that the site of immediate glucose disposal is skeletal muscle. See Katz L. D., Glickman M. G., Rapoport 5, Ferrannini E., De Fronzo R. A., *Splanchnic and Peripheral Disposal of Oral Glucose in Man.* Diabetes 1983; 32:675. The failure of glucose storage to be activated in Type 2 diabetics during the administration of carbohydrate leads to reduced tissue uptake of glucose and may be a major defect leading to insulin resistance. See Lillioja 5, Mott D. M., Zawadzki J. K., Young A. A., Abbott W. G., Bogardus C., *Glucose Storage is a Major Determinant of in Vivo "Insulin Resistance" in Subjects with Normal Glucose Tolerance.* J Clin Endoc Metab 1986; 62:922–927.

2. Defect in insulin release—However, a defect in insulin storage or release is also involved, because massively obese people with marked insulin resistance usually do not have hyperglycemia or diabetes mellitus. See, Wajngot A., Roovete A. et al., *Insulin Resistance and Decreased Insulin Response to Glucose in Lean Type 2 Diabetics.* Proc Natl Acad Sci USA 1982; 79:4432–4436. This finding suggests that the normal pancreas has sufficient reserve to compensate for insulin resistance imposed by obesity or other factors while the pancreas in Type 2 subjects does not. In this sense, therefore, the primary defect can be considered to be a dysfunctional islet $\beta$-cell, although the abnormality would not be recognized without the additional symptom of insulin-resistance. It may be that those patients with non-obese Type 2 have a more severe defect in insulin release.

The nature of the islet $\beta$-cell lesion in Type 2 diabetes is unclear. Unlike those in Type 1 diabetes, the Type 2 $\beta$-cells retain the ability to synthesize and secrete insulin, as evidenced by the presence of insulin and C-peptide both in these cells and circulating in the plasma. Available studies suggest that there is a modest reduction in the numbers of $\beta$-cells, but this is insufficient to account for the observed reduction in insulin secretion. Stefan Y., Orci L., et al., Diabetes 1982; 31:694–700. It has therefore been thought to be likely that the remaining $\beta$-cells have impaired function, manifested as a delay in the initial secretion of insulin in response to a glucose load, even in the earliest detectable stage of the disease, and by the fact that in Type 2 diabetics, less insulin is secreted at any glucose concentration in both overtly diabetic subjects and in those with clinically latent forms of the disease.

The primary aim of treatment in all forms of diabetes mellitus is the same, namely the reduction of blood glucose levels to as near normal as possible, thereby minimizing both the short- and long-term complications of the disease. Tchobroutsky G., *Relation of Diabetic Control to Development of Microvascular Complications.* Diabetologia 1978; 15:143–152.

The treatment of Type 1 diabetes necessarily involves the administration of replacement doses of insulin, administered by the parenteral route. In combination with the correct diet and self-blood glucose monitoring, the majority of Type 1 patients can achieve reasonable control of blood glucose. Treatment of Type 2, in contrast to the treatment of Type 1 frequently does not require the use of insulin. Therapy may be based on diet and lifestyle changes, augmented by therapy with oral hypoglycemic agents (sulfonylureas or biguanides).

Modification of the diet and lifestyle is the first line of therapy in Type 2. If obesity is present, it is also necessary to reduce body weight to near-ideal levels. Important features of the diabetic diet include an adequate but not excessive total calorie intake, with regular meals; restriction of the content of saturated fat; a concomitant increase in the polyunsaturated fatty acid content; and, an increased intake of bound carbohydrate ("dietary fiber"). A second important lifestyle modification is the maintenance of regular exercise, as an aid both to weight control and also to reduce the degree of insulin resistance.

Thus, institution of therapy in Type 2 usually involves a trial of dietary therapy, typically for six to twelve weeks in the first instance. If after an adequate trial of diet and lifestyle modification, fasting hyperglycemia persists, then a diagnosis of "primary diet failure" may be made, and either a trial of oral hypoglycemic therapy or direct institution of insulin therapy will be required to produce blood-glucose control and, thereby, to minimize the complications of the disease. It must be noted that although weight loss is the aim of lifestyle and dietary modification, it is, of course, frequently not achieved.

Type 2 diabetics that fail to respond to diet and weight loss may respond to therapy with sulfonylureas. The sulfonylureas comprise a class of drugs originally derived from the sulfonamide, p-aminobenzene-sulfonamido-isopropylthiadiazole. The class of sulfonylurea drugs includes Acetohexamide, Chlorpropamide, Tolazamide, Tolbutamide, Glibenclaminde, Glibornuride, Gliclazide, Glipizide, Gliquidone and Glymidine. These drugs act primarily by augmenting residual pancreatic beta-cell function and are relatively easy to use. It is important to understand, however, that all sulfonylureas may lead to hypoglycemic reactions, including coma, four or more hours after meals. Indeed, hypoglycemic episodes may last for several days so that prolonged or repeated glucose administration is required. Reactions have occurred after one dose, after several days of treatment, or after months of drug administration. Most reactions are observed in patients over 50 years of age, and they are more likely to occur in patients with impaired hepatic or renal function. Overdosage, or inadequate or irregular food intake may initiate hypoglycemia. Other drugs can increase the risk of hypoglycemia from sulfonylureas including other hypoglycemic agents, sulfonamides, propranolol, salicylates, phenylbutazone, probenecid, dicumarol, chloramphenicol, monoamine oxidase inhibitors, and alcohol.

Additionally, it is understood that sulfonylureas should not be used in patients with hepatic or renal insufficiency because of the importance of the role of the liver in their metabolism and the kidney in the excretion of the drugs and their metabolites. Furthermore, these compounds are best avoided in obese patients unless their symptoms and diabetic control have not improved despite weight loss to within 15 percent of their ideal bodyweight, as they tend to encourage weight gain.

The suggestion has also been made that sulfonylureas may cause an increase in morbidity and mortality from coronary artery disease. See University Group Diabetic Programme. *A Study of the Effects of Hypoglycemic Agents on Vascular Complications in Patients with Adult-onset Diabetes.* Diabetes 1976; 25:1120-1153. That study has been criticized for analyzing data according to the treatment groups to which patients were assigned, regardless of adherence to therapy. Critics have suggested that patients given insulin in variable dosage to optimize glucose control might have had a decrease in cardiovascular mortality (see Kilo C., Williamson J. R., Choi S. C., Miller J. P., *Refutina the University Group Diabetic Programme Conclusion that Insulin Treatment Does Not Prevent Vascular Complications in Diabetes.* Adv Exp Med Biol 1979; 119:307-311), and that the drug Tolbutamide might only be associated with increased mortality if the fasting blood glucose remains above 11.1 mmol/L. Kilo C., Miller J. P., Williamson J. R., *The Crux of the University Group Diabetic Programme. Spurious Results and Biologically Inappropriate Data Analysis.* Diabetologia 1980; 19:179-185. Nevertheless, and in spite of the availability of therapy with oral agents, the rate of morbidity and mortality from coronary artery disease in Type 2 populations remains considerably higher than that in non-diabetics.

Another group of compounds, the biguanides, was developed independently of the sulfonylureas. Of the three antidiabetic biguanides, which include phenformin, only metformin is useful in treating Type 2 diabetes with a lesser risk of side-effects when applied in a well controlled regimen. See Schafer G., *Biguanides. A Review of History, Pharmacodynamics and Therapy.* Diabetes et metabolism 1983; 9:148-163. Metformin does not cause an increase in insulin secretion, but is thought to exert its hypoglycemic effect mainly by increasing peripheral glucose utilization. Like the sulfonylureas, however, it is only effective in diabetics with a degree of residual endogenous insulin secretion and, therefore, it presumably acts by increasing the sensitivity of peripheral tissues to insulin. Other metabolic effects of metformin which are believed to contribute to its antidiabetic action include: 1) the induction of intestinal malabsorption of glucose and other nutrients; 2) the inhibition of increased hepatic and renal gluconeogenesis; and 3) the inhibition of lipolysis and free fatty acid oxidation. Unlike insulin, however, metformin does not encourage lipogenesis. It is most frequently used in overweight diabetics who cannot, or will not, lose weight. Metformin does not exert a hypoglycemic action in non-diabetic subjects.

Because of the real and unpredictable risk of the frequently fatal complication of lactic acidoses, use of the biguanide phenformin has been discontinued. Metformin is not free from this hazard, however, and the decision to use it in therapy must therefore be taken with care, and only in those patients who have undergone primary dietary failure, and who either are overweight or have also undergone "secondary sulfonylurea failure" (and are overweight). It is recommended that metformin not be given to patients with renal disease or a history of alcohol abuse, and its use must immediately be stopped if nausea, vomiting, diarrhea or any intercurrent illness appears.

It is noteworthy that, notwithstanding the above-noted avenues of treatment, insulin therapy remains the treatment of choice for many patients with Type 2 diabetes, especially those who have undergone primary diet failure and are not obese, or those who have undergone both primary diet failure and secondary oral hypoglycemic failure. But it is equally clear that insulin therapy must be combined with a continued effort at dietary control and lifestyle modification, and in no way can be thought of as a substitute for these. In order to achieve optimal results, insulin therapy should be followed with self-blood glucose monitoring and appropriate estimates of glycosylated blood proteins. Insulin may be administered in various regimens alone, two or multiple injections of short, intermediate or long acting insulins, or mixtures of more than one type. The best regimen for any patient must be determined by a process of tailoring the insulin therapy to the individual patient's monitored response.

The trend to the use of insulin therapy in Type 2 diabetes has increased with the modern realization of the importance of strict glycemic control in the avoidance of long-term diabetic complications. In non-obese Type 2 diabetics with secondary oral hypoglycemic failure, however, although insulin therapy may be successful in producing adequate control, a good response is by no means assured. See, e.g., Rendell M., Slavin D., Meltz G., Simpson J., Barquet A., *A Case of Maturity-onset Diabetes Mellitus Resistant to Insulin but Responsive to Tolbutamide.* Ann Int Med 1979; 90:195-97. In one study, only 31 percent of 58 non-obese patients who were poorly controlled on maximal doses of oral hypoglycemic agents achieved objectively verifiable improvement in control on a simple insulin regimen. See Peacock I., Tattersall R. B., *The Difficult Choice of Treatment for Poorly Controlled Maturity-onset Diabetes: Tablets or Insulin.* Br Med J 1984; 288:1958-1959. In obese diabetics with secondary failure, the picture is even less clear-cut because in this situation insulin frequently increases body weight, often with a concomitant deterioration in control.

It will be apparent, therefore, that the current state of knowledge and practice with respect to the therapy of Type 2 diabetes is by no means satisfactory. The majority of patients undergo primary dietary failure with time, and the majority of obese Type 2 diabetics fail to achieve ideal body weight. Although oral hypoglycemic agents are frequently successful in reducing the degree of glycemia in the event of primary dietary failure, many authorities doubt that the degree of glycemic control attained is sufficient to avoid the occurrence of the long term complications of atheromatous disease, neuropathy, nephropathy, retinopathy and peripheral vascular disease associated with longstanding Type 2 diabetes. The reason for this can be appreciated in the light of the current realization that even minimal glucose intolerance, approximately equivalent to a fasting plasma glucose of 5.5 to 6.0 mmol/L, is associated with an increased risk of cardiovascular mortality. See Fuller J. H., Shipley M. J., Rose G., Jarrett R. J., Keen H., *Coronary Heart Disease Risk and Impaired Glucose Tolerance*. The Whitehall study. Lancet 1980; 1:1373-1378. It is also not clear that insulin therapy produces any improvement in long-term outcome over treatment with oral hypoglycemic agents. Thus, it can be appreciated that a superior method of treatment would be of great utility. Such a method, and compounds useful therefor, are described and claimed herein.

SUMMARY OF THE INVENTION

The invention provides compounds, pharmaceutical compositions and methods for treatment of type 2 diabetes using hypoglycemic agents together with agents useful in the regulation of the effects of amylin, a hormone isolated from the pancreatic amyloid masses typically found in Type 2 diabetics. We have found that amylin leads in elevated amounts to abnormal insulin release and abnormal glycogen synthesis, and we have determined that amylin is elevated by therapy with standard hypoglycemic agents. When used in conjunction with hypoglycemic therapy, amylin regulation can be accomplished, for example, by blocking the binding of amylin and/or calcitonin gene related peptide (CGRP) and/or other amylin agonists, or biologically active sub-peptides of amylin or CGRP, by the use of inhibitors including substituted or altered peptides or subpeptides of amylin or CGRP, or by the regulation of the expression or production or release of amylin or CGRP, or active sub-peptides thereof.

In conjunction with the treatment of patients with hypoglycemic agents, especially those which lead to enhanced amylin levels, chemical antagonists to amylin which bind to the amylin receptor without triggering a response can also be used to reduce the effects of amylin or amylin agonists (including CGRP) or biologically active subpeptides thereof which act to inhibit the body's basal and insulin-stimulated responses to glucose, or to prevent the interference of those molecules with insulin release. Thus, unamidated amylin, the substituted $ser^2$, $ser^7$ peptides and subpeptides of amylin and CGRP described and claimed herein, including amylin 8-37 and CGRP 8-37, can be used to ameliorate insulin resistance in muscle. Other competitive antagonists include cross-linked amylin agonists (including amylin, CGRP and active subpeptides thereof) and synthetic amylin. Direct blockage of the amylin receptor can also be accomplished with monoclonal antibodies and anti-idiotype antibodies. Other chemical antagonists to amylin and amylin agonists include organic compounds which can be assayed and/or screened for anti-amylin effects by methods disclosed herein. Assays and screening methods which enable the evaluation and identification of compounds which affect amylin secretion are also disclosed. Noncompetitive amylin antagonists include antibodies directed to the active sites of amylin and CGRP.

The invention particularly provides for methods for the treatment of non-insulin dependent, or type II, diabetes mellitus in a patient, which comprises the administration to said patient of a hypoglycemic agent that enhances plasma concentrations of amylin, said hypoglycemic agent being administered in conjunction with a therapeutically effective amount of an amylin antagonist. The hypoglycemic agents include the sulfonylurea hypoglycemic agents, including those sulfonylurea hypoglycemic agents which also enhance plasma concentrations of insulin, such as first and second generation sulfonylurea agents including glibenclamide and tolbutamide. The invention also provides for methods for enhancing the blood glucose lowering effects of a hypoglycemic agent by the administration of an amylin antagonist in conjunction with hypoglycemic agents that, when administered for said treatment, result in increased circulating levels of amylin. The hypoglycemic agents and the amylin antagonists may be administered together or separately.

The invention also provides a method for determining patients or subgroups of patients in whom sulfonylurea hypoglycemic agents cause enhanced plasma concentrations of amylin, which comprises the administration to a patient or patients of an effective amount of said sulfonylurea hypoglycemic agent, and the assessment of plasma amylin concentrations in said patient or patients at a predetermined time or times. This assessment can be carried out by the use of amylin assays, including binding assays, biological assays, chemical assays and other separation assays. Additionally, a method for monitoring or evaluating the treatment of a patient with hypoglycemic therapy is provided, in which the assessment of plasma amylin concentration in said patient at a predetermined time or times is carried out by the use of an amylin assay following the administration to said patient of an effective amount of hypoglycemic agent. Hypoglycemic agents which can be so monitored include the sulfonylurea hypoglycemic agents. The amylin assays useful in this method are those mentioned above, but particularly preferred is an amylin immunoassay. The amylin immunoassay used may be qualitative, semi-quantitative, or quantitative. This method for monitoring or evaluating the treatment of a patient with hypoglycemic therapy will be particularly advantageous for those hypoglycemic agents that do not enhance amylin levels, such as the biguanide metformin.

Pharmaceutical compositions that include therapeutically effective amounts of a hypoglycemic agent that enhances plasma concentrations of amylin and an amylin antagonist are also provided. The invention also provides a method for evaluating or screening for agents that may be useful in the treatment of conditions associated with hypoglycemia wherein one or more of said agents are brought together with a biological system by which amylin levels can be monitored and the effect of said agent or agents on the levels of amylin in said biological system are evaluated. Appropriate biological systems include whole animals, cell culture, and the perfused pancreas system. Specially preferred cell cultures are islet beta cell cultures, particularly the HIT T-15 cells. These methods can be used to batch screen putative hypoglycemic agents and those that are desired for further screening can be evaluated again in the same or a different biological system.

The invention also provides for a method of evaluating or screening for agents that may be useful in the treatment of conditions associated with hyperamylinemia, in which said agent or agents are brought together with a biological system by which amylin levels can be monitored, and the effect of said agent or agents on the secretion of amylin in said biological system is determined. In this method, furthermore, the effect on basal and/or segretagogue-stimulated secretion of amylin can be evaluated, as can the effect of said agent or agents on the secretion of insulin. Preferred biological systems for the evaluation of agents that effect amylin secretion is the cell culture, particularly an islet beta cell culture such as the HIT T-15 cells.

DETAILED DESCRIPTION OF THE INVENTION

A. Pancreatic Amyloid

Figure 1:
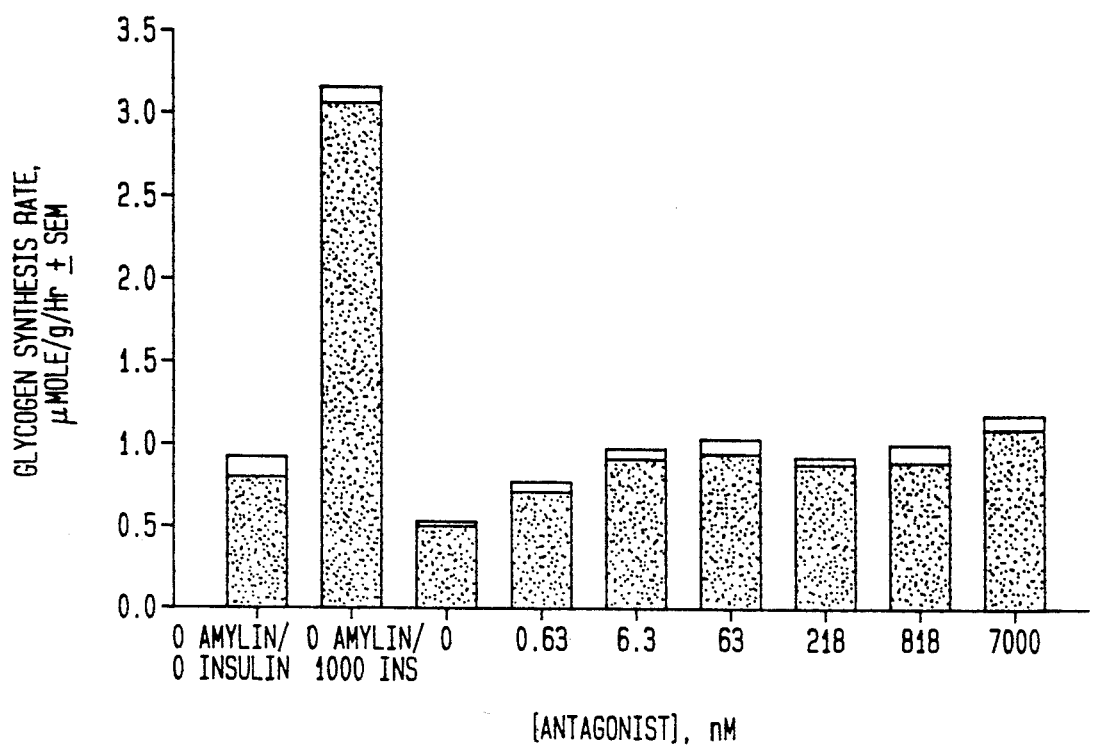
FIG. 1 shows the effects of an amylin antagonist on the inhibitory effect of amylin on insulin-stimulated muscle glycogen synthesis.

Amyloid is the name given to extracellular deposits of twisted-helical, paired protein filaments formed from anti-parallel beta-pleated sheets of identical polypeptide subunits See Glenner G. G., *Amyloid Deposits and Amyloidosis; The Beta-fibrilloses.* N Engl J Med 1980; 302:1283-1292. A deposit of amyloid material, islet amyloid, is frequently found in the pancreases of patients with Type 2 diabetes mellitus. See Clark A. Cooper G. J. S. et al., *Islet Amyloid Formed from Diabetes-Associated Peptide May Be Pathogenic in Type II Diabetes.* Lancet 1987; 2:231-234. In Type 2 diabetics, some workers have reported deposits of islet amyloid in more than 90 percent of the islets of Langerhans, bodies comprising clusters of endocrine-secreting cells scattered throughout the substance of the pancreas. These deposits can occupy up to four-fifths of the islet and are associated with a loss of B-cells and B-cell density. See Westermark P. Wilander W., Diabetologia 1970; 15:417–421.

Studies have indicated that the number of islets affected and the extent of amyloid deposition increases with the degree of hyperglycemia in humans (see Schneider H. M., Storkel S. Will H. M., *Das Amyloid der Langerhansschen Insulin und Selne Bezlehung Bum Diabetes Mellitus.* Dt Med Wschr 1980; 105:1143–1147) and in Type 2 diabetic Macaca bra monkeys. See Howard C. F., *Longitudinal Studies on the Development of Diabetes in Individual Macaca nigra.* Diabetologia 1986; 20:301–306. It has also been shown that the amount of islet amyloid in humans increases as does the severity of Type 2 diabetes, as judged by the need for insulin therapy, such that 100 percent of a series of insulin-treated Type 2 diabetics had significant islet amyloid. See Maloy et al., *The Relation of Islet Amyloid to the Clinical Type of Diabetes.* Human. Pathol. 1981; 12:917-922. The prevalence of islet amyloid in the Type 2 diabetic population is higher than that in the non-diabetic population. Bell, E. T., *Hyalinzation of the Islets of Langerhans in Nondiabetic Individuals,* Am. J. Path. 1959; 35:801–05. This has lead to the hypothesis that islet amyloid itself might be a factor leading to the abnormal insulin secretion in Type 2 diabetes. See Clark et al. Lancet 1987; 2:231–234.

Chemical analysis of islet amyloid has previously been frustrated by the insolubility and small amounts of the amyloid in the pancreas as a whole. Recently, a partial description of an impure peptide deposited in amyloid fibrils in an insulin expressing tumor of the islets of Langerhans (an "insulinoma") was reported. See Westermark P. Wernstedt C. Wilander E. Sletten K., *A Novel Peptide in the Calcitonin-Gene-Related Family as an Amyloid Fibril Protein in the Endocrine Pancreas.* Biochem Biophys Res Comm 1986; 140:827-831. The peptide described therein appears to be very impure (no more than about 10% pure) and, in fact, only eighteen residues could be identified. Subsequent studies, presumably on the same impure preparation, resulted in the identification of thirty-six out of thirty-seven residues of a peptide. The residue at position thirty-six could not be identified and it was suggested in the second report that two other residues were different from those previously reported. See Westermark P., Wernstedt C., Wilander E., Hayden D. W., O'Brien T. D. and Johnson K. H., *Amyloid Fibrils in Human Insulinoma and Islets of Langerhans of the Diabetic Cat are Derived from a Neuropeptide-like Protein also Present in Normal Islet Cells.* Proc Natl Acad Sci USA 1987; 84:3881-3885. Westermark et al. designated the peptide "Insulinoma Amyloid Polypeptide", or IAP, and subsequently IAPP, "Insulinoma (or Islet) Amyloid Polypeptide."

B. The Amylin Hormone

Cooper et al. reported the purification and complete characterization of a peptide from amyloid masses extracted from human Type 2 diabetic pancreases. The amino acid at position 36 was unequivocally identified as threonine in separate isolates of the peptide from two diabetic pancreases. See Cooper G. J. S., Willis A. C., Clark A., Turner R. C., Sim R. B., Reid K. B. M., *Purification and Characterization of a Peptide from the Amyloid-rich Pancreases of Type 2 Diabetic Patients.* Proc Natl Acad Sci USA 1987; 84: 8628-8632. This peptide was shown to be highly pure (more than 90% pure) on the basis of the comparison between sequencer yields and the results of quantitative protein analysis on samples of purified peptide. Cooper et al. designated the peptide "Diabetes Associated Peptide", noting that it is present in extracts from diabetic subjects but absent from equivalent extracts from non-diabetic subjects. Diabetes Associated Peptide ("DAP") is the subject of United Kingdom Patent Application No. 8709871 (entitled "Peptides") filed on Apr. 27, 1987, and corresponding U.S. applications filed Apr. 27, 1988, Nov. 23, 1988, and May 2, 1989, and the use of the peptide in isolation or in conjunction with insulin for the treatment of diabetes mellitus is the subject of United Kingdom Patent Application No. 8720115 (Entitled "Treatment of Diabetes Mellitus") filed on Aug. 26, 1987 by G. J. S. Cooper and M. S. Cameron, and filed in the United States on Aug. 26, 1988.

DAP is characterized as a peptide having the following amino acid sequence:

```
1              5                    10        [1]
Lys—Cys—Asn—Thr—Ala—Thr—Cys—Ala—Thr—Gln—

11             15                   20
Arg—Leu—Ala—Asn—Phe—Leu—Val—His—Ser—Ser—

21             25                   30
Asn—Asn—Phe—Gly—Ala—Ile—Leu—Ser—Ser—Thr—

31             35
Asn—Val—Gly—Ser—Asn—Thr—Tyr—NH2
```

Cooper et al. demonstrated that the native molecule contains a disulfide bridge between the Cys residues shown at positions 2 and 7 in the primary structure of DAP, is amidated at the 3' end, and is formed as a propeptide, i.e, amylin plus the N-terminal amino acid sequence comprising TPIESHQVEKR, KR being the processing signal. Our secondary structural prediction analysis of the amino acid sequence by the methods of Chou and Fasman, and of Kyte and Doolittle (see Chou, P. Y. Fasman, G. D. Annu. Rev. Blachem. 1978; 47:251-276 and Kyte, J., Doolittle, R. F. J. Mol. Biol. 1982; 157:105-132) further indicates that the middle portion of the molecule, in particular that portion lying between residues 18 and 27, is likely to be responsible for the formation of the islet amyloid masses, as this portion of the molecule is hydropathic and has a strong tendency to beta-sheet formation. We have experimentally confirmed this tendency, within the stated portion of the molecule, to form insoluble aggregates. We have also detected DAP in normal pancreatic tissue, albeit at lower concentrations.

Because DAP has been isolated from amyloid masses in the pancreas and because of its role as a receptor-mediated hormone, as discussed below, for the purposes of this invention, DAP will be referred to herein as "amylin". The amylin subpeptide [2], shown below, is amyloidogenic (that is, it possesses the tendency to form amyloid):

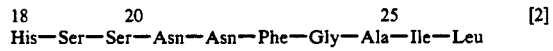

```
18         20                  25            [2]
His—Ser—Ser—Asn—Asn—Phe—Gly—Ala—Ile—Leu
```

We have further discovered that amylin is at least bifunctional and that two of the biological effects of the molecule are that (1) it causes B-cells within the islets of Langerhans (insulin producing cells) to release less insulin in the presence of amylin than they do in the absence of amylin, and (2) it causes a major reduction in both basal and insulin-stimulated glycogen synthesis in skeletal muscle, by causing the muscle cells to ignore the insulin signal.

We discovered that these activities are present in different portions of the molecule. We determined that one active site of the peptide is located in the C-terminal region occupying positions 27-37 of the peptide as indicated by the underlining of residues 27-37 in the above diagram of the complete amylin molecule [1]. This was demonstrated in Example 4 below by the inhibition of the release of insulin by pancreatic-islet B-cells after a glucose challenge following treatment of isolated islets of Langerhans with the amylin subpeptide amylin 27-37. In the same Example is shown the identical effect using the subpeptide CGRP 27-37, which we believe affects the amylin receptor as an agonist, as does whole CGRP.

We have also discovered that the N-terminal portion of amylin works to prevent the processing of glucose into glycogen, a process which is normally markedly stimulated by insulin. This was demonstrated by inhibition of activity of the skeletal muscle enzyme glycogen synthase as determined by demonstration of a reduction in the amount of incorporation of radioactively-labelled glucose into glycogen in rat soleus muscle with amylin and amylin subpeptides in Examples 1 and 2 below.

In essence, we believe that in normal concentrations amylin is part of a control system which reduces the action of insulin to increase carbohydrate uptake into skeletal muscle (and hence storage into glycogen), with the secondary effect of preventing hypoglycemia when insulin concentrations become excessive in relation to circulating glucose levels. Cooper G. J. S., Cameron M. S. "Treatment of Diabetes Mellitus". United Kingdom Patent Application No. 8720115; Aug. 26, 1987. The biological activity of amylin is a newly discovered endocrine homeostatic mechanism whereby the body is able to control the distribution of carbohydrate energy (as glucose) according to minute to minute requirements.

The mechanism can best be thought of as complementary to the insulin-mediated control of glucose storage as glycogen in skeletal muscle. It appears that amylin works via a receptor-mediated mechanism which serves to control the activity of glycogen synthase, probably in a way analogous to the functioning of the insulin receptor through secondary intracellular messenger molecules (see Czech M. P., *The Nature and Regulation of the Insulin Receptor Structure and Function*. Ann Rev Physiol 1985; 47:357–381 and Espinal J., *Mechanisms of Insulin Action.* Nature 1987; 328:574–575) and thereby controls the incorporation of glucose into glycogen.

C. Sulfonylurea Hypoglycemic Agents and Amylin

Included among the so-called "first generation" sulfonylureas are four compounds, long available in the United States, which reportedly have similar mechanisms of action, i.e., stimulation of the islet tissue to secrete insulin. *Joslin's Diabetes Mellitus, Chapter* 21 (12th ed. 1985); *Goodman and Gillman's: The Pharmacological Basis of Therapeutics,* page 1504 (7th ed. 1988). These four compounds are tolbutamide, chlorpropamide, acetohexamide and tolazamide. As shown below, the basic functional parts of the sulfonylurea compounds are a benzene ring, a sulfonyl group, and a urea:

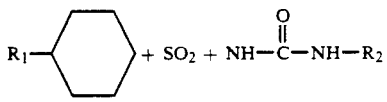

With tolbutamide, a methyl group is added to the para-position of the benzene ring and a butane to the urea group. For chlorpropamide, chloride is attached in the para-position of the benzene ring and a propane group added to the urea. For acetohexamide, an acetyl group is placed at the para-position of the benzene ring and a cyclohexane radical added to the urea. For tolazamide, methyl is at the para-position as in tolbutamide but, instead of a butane, a hexhydroazepinyl group is added to the urea group. The effective sulfonylurea compounds are arylsulfonylureas with substitutions on the benzene and urea groups.

It is believed that the primary action of the sulfonylurea agents is to stimulate insulin release, because functioning pancreatic islets are needed for the effectiveness of these compounds. Although there has been disagreement as to whether the insulin output is actually increased, the release is at least triggered. *Joslin's Diabetes Mellitus, supra* at 419–420. Extrapancreatic actions may also be important in the activity of these drugs, but knowledge of the exact nature of these effects is incomplete.

By definition, the "second generation" sulfonylurea agents are those recently developed, about 25 years after the original compounds, and they are reported to have the same general mode of action as the earlier sulfonylurea agents. Id. at 437. The second generation compounds are said, however, to be more efficient and effective in smaller doses. There are about a dozen agents in this category and they include glibenclamide and glipizide, as well as gliclacide.

In recent years, it has become apparent that deposition of amylin-containing amyloid within the isletes of Langerhans (islet amyloid) is the mechanism whereby decompensating of the islets is induced in most type 2 diabetics. Cooper et al., Proc. Natl. Acac. Sci. USA 1987; Cooper et al., Proc. Natl. Acad. Sci. USA, 1988; Cooper et al.; Biochem. Biophys. Acta, 1989. It is also believed that excessive production of amylin from the islet β-cell is the metabolic event leading to slow accumulation of this peptide as islet amyloid, which ultimately results in failure of the islet to secrete appropriate amounts of insulin in response to glucose. Excessive production of amylin from the pancreas is also responsible for the insulin resistance seen in patients with impaired glucose tolerance, obesity, and early type 2 diabetes mellitus. See Cooper et al., Proc. Natl. Acad. Sci. USA, 1988; Leighton & Cooper, Nature, 1988; Cooper et al., Biochem. Biophys. Acta, 1989; Molina et al., Diabetes, 1990.

As noted, the sulfonylurea drugs are oral agents widely used in the therapy of type 2 diabetes. However, up to 40% of patients fail to respond to these drugs. Their use is also frequently complicated by progressive failure in their effectiveness over a period of time. This problem (so-called "secondary failure") is a common problem of previously unknown causation which complicates the sulfonylurea therapy of NIDDM. Shafir E., Bergman M., Felig P. (1987) *The Endocrine Pancreas: Diabetes mellitus.* In Endocrinology and Metabolism, 2d Ed., Felig P., Baxter J. D., Broadus A. E. & Frohman L. A. Eds., McGraw-Hill, New York, N.Y.

We further disclose herein the beneficial use of sulfonylurea drugs in conjunction with amylin antagonist therapy. Using a system comprising a continuous islet β-cell line and immunoassays specific for amylin and insulin, we have discovered that both first generation (e.g., tolbutamide) and second generation (e.g., glibenclamide) sulfonylurea drugs stimulate the secretion of amylin from islet β cells in a dose dependent fashion, in the presence of either 0 or 10 mM glucose. See Example 7 below. In the same series of experiments, metformin was shown not to influence insulin (or amylin) secretion at all over the concentration range examined. In this series of experiments, observed effects of the sulfonylureas on insulin secretion were consistent with previously observed effects in similar systems.

These unexpected discoveries have fundamental implications for the use of sulfonylureas in the therapy of diabetes mellitus. The phenomenon of secondary failure of sulfonylurea therapy, while its cause is heretofore unknown, is associated with a progressive incapacity of the islet β-cells to respond to therapy with continued secretion of insulin. We believe the cause of the progressive reduction in insulin response in NIDDM is directly related to islet amyloid deposition with progressive loss of β-cell mass (Cooper et al., Biochem. Biophys. Acta, 1989). This process is stimulated by the increased amylin secretion present in insulin resistant states.

Furthermore, and importantly, we have now shown that sulfonylurea treatment induces further increased amylin secretion from isolated pancreatic β-cells in the presence or absence of glucose. These findings support the determination that sulfonylurea treatment of humans leads to increased rates of amylin secretion and therefore amyloid deposition in the pancreas, with resulting loss of pancreatic β-cells and the onset of β-cell failure. Non-insulin-dependent patients with high amylin (or insulin) levels are liable to react adversely to sulfonylurea therapy by acceleration of their rates of amyloid deposition and islet-cell failure. Patients with this condition must therefore be monitored for blood amylin levels before and after they are commenced on sulfonylurea therapy. Should pre-treatment amylin levels be high, or should these levels respond excessively to sulfonylurea therapy, then sulfonylurea therapy may be contraindicated or, alternatively, should be accomplished in conjunction with amylin antagonist treatment.

Contrastingly, metformin does not influence rates of amylin secretion from the islet β-cells. Therefore, metformin therapy may be indicated in the presence of high insulin or amylin levels in NIDDM. It is to be expected that therapy with metformin will not accelerate the rate of pancreatic decompensation as rapidly as sulfonylureas.

Example 8 shows that physiological concentrations of glucose and arginine stimulated amylin and insulin secretion from pancreatic islet beta cells in a dose-dependent manner. The rates of secretion of the two hormones were strongly correlated. Arginine also potentiated glucose-stimulated amylin and insulin secretion from the HIT cells. Glucagon enhanced both amylin and insulin secretion in a dose-dependent fashion. Differences in glucagon-stimulated secretion rates resulted in a decrease in the molar amylin insulin ratio with increasing glucagon concentrations. Somatostatin suppressed both amylin and insulin release from HIT cells in a co-ordinated, dose-dependent fashion. These results demonstrate the unexpected fact that HIT islet beta cells secrete amylin, as well as insulin, in response to typical nutrient stimuli and known paracrine modulation of islet beta cell function, thus providing a useful method for the evaluation and/or screening for compounds that modulate amylin and/or insulin secretion, as described.

D. Amylin Activities

Utilizing in vitro methods we have found that isolated rat skeletal muscle tissue presented with insulin and radioactive glucose showed a decrease in glycogen synthesis at all physiological concentrations in the presence of amylin, and certain amylin subpeptides, compared with control experiments in which those amylin compounds were not present. These unexpected findings were confirmed as described in Examples 1 and 2, infra with:

1) whole synthetic amylin (residues 1-37, unamidated, synthesized chemically by the method of Barany and Merrifield (1979). "Solid phase synthesis" in Grass, E. Melenhater, J. eds. *The Pentides*. Academic Press New York, N.Y.);

2) whole native amylin extracted from a diabetic human pancreas and purified according to the method of Cooper G. J. S. et al. See Cooper G. J. S., Willis A. C. et al. Proc. Natl Acad Sci USA, supra, in which the identity of the molecule was determined by amino acid sequencing according to the Edman method on an Applied Biosystems 470A protein sequencer (see Herrick, C. M., Hunkapiller, M. W. Dreyer, W. J. J. Biol. Chem. 1981; 256:7990-7997) using the 02CPTH cycle in the Version 2.0 software (Applied Biosystems, Foster City, Calif.); and 3) with various subpeptides (identified as subpeptides [3J-[5J below) corresponding to that portion of amylin comprising the first 16 residues (with and without the 2-7 disulfide bridge), and residues 8-37, all chemically synthesized according to the method of Barany and Merrifield, Subpeptides [3] and [4] in which activity in reducing the incorporation of radioactive glucose into glycogen was demonstrated were as follows:

```
                            [3]
        ┌─────────────────┐
     1  │     5           │   10
    Lys—Cys—Asn—Thr—Ala—Thr—Cys—Ala—Thr—Gln
    11              15
    Arg—Leu—Ala—Asn—Phe—Leu

Lys—Cys—Asn—Thr—Ala—Thr—Cys—Ala—Thr—Gln—   [4]
    11              15
    Arg—Leu—Ala—Asn—Phe—Leu
```

The subpeptide [5], corresponding to the 8the to the 37th residues of amylin, also reduced the incorporation of radioactive glucose into glycogen, and is shown below:

```
            10                 15              20      [5]
    Ala—Thr—Gln—Arg—Leu—Ala—Asn—Phe—Leu—Val—His—Ser—Ser 25              30
           Asn—Asn—Phe—Gly—Ala—Ile—Leu—Ser—Ser—Thr

35
               Asn—Val—Gly—Ser—Asn—Thr—Tyr
```

Amylin peptides in which no activity in reducing the insulin-stimulated incorporation of radioactive glucose into glycogen in isolated rat skeletal muscle in vitro included the following subpeptides [6] and [7], i.e., amylin 27-37, and ser$^2$, ser$^7$ amylin 1-16:

```
    27      30              35                  [6]
    Leu—Ser—Ser—Thr—Asn—Val—Gly—Ser—Asn—Thr—Tyr 1           5               10              [7]
    Lys—Ser—Asn—Thr—Ala—Thr—Ser—Ala—Thr—Gln
    11              15
    Arg—Leu—Ala—Asn—Phe—Leu
```

In subpeptide [7], the SH-group containing Cys residues at positions 2 and 7 were replaced by hydroxyl-group containing Ser residues.

The results with subpeptides [3]-[7] indicated that the presence of the Cys residues in positions 2 and 7 is necessary for activity in the molecule, and that there is residual activity present in the absence of an intact Cys(-2)-Cys(7) disulfide bond.

We further demonstrated, as shown in Example 4 below, that the subpeptides amylin 27-37 and CGRP 27-37 can act to reduce the amount of insulin produced by the islets of Langerhans in response to a standard glucose challenge.

As further described in Example 5 below, we have also shown that amylin acutely produces diabetes (fasting hyperglycemia greater than 140 mg/dL) when administered in vivo by intravenous injection.

E. Amylin Antagonists

Significantly, the amylin peptide itself can be used to prepare compounds that tend to neutralize or impede its activity, for example, by reduction of the disulfide, deamidation or the use of proamylin and, thus, to treat Type 2 diabetics. One approach relates to identification of the active site or sites of the amylin molecule, followed by the alteration of those active sites of the amylin peptide sequence, by substitution of amino acids within the active site by other amino acids, so that the peptide does not lose its binding affinity for the receptor site, but upon binding is unable to promote activity, and thereby blocks the effect of amylin. This approach can be applied to the C-terminal active sites of amylin and CGRP, namely amylin 27-37 and CGRP 27-37, and has already been demonstrated with the N-terminal active site of amylin, that portion of the molecule which is active in inducing an inhibition of the rates of basal and insulin-stimulated glycogen synthesis in muscle. Thus, we have shown in Example 3 below that the substituted subpeptide $ser^2$, $ser^7$ amylin 1-16, subpeptide [6] above, ameliorates the amylin effect in muscle. Other substituted antagonists include $ser^2$, $ser^7$ amylin, $ser^2$, $ser^7$ CGRP and $ser^2$, $ser^7$ CGRP 1-16. Substitution of chemically altered amino acid residues within the active regions of the peptides or subpeptides will also accomplish the objective of maintaining binding affinity without resulting activity. The incorporation of chemically altered residues into the amylin or CGRP active sites can be accomplished by incorporating chemically altered, activated residues into the synthetic protocol described herein. Target residues for substitution include those at amino acid position 2-7, 9, 11-13, 15, 16, 30-34 and 37. As shown in Example 6 below, unsubstituted subpeptides also show antagonist action.

Crystallographic analysis of the structure of amylin, and of amylin co-crystalized with its receptor, or part of its receptor, will allow analysis of the interactions between amylin and its receptor. Such analysis will allow the determination of those residues which are of primary importance in the interaction between amylin and its receptor, and will in turn indicate which residues should be changed in order to produce an effective antagonist. The structural analysis of the amylin-amylin receptor interaction will also allow the determination of the likely molecular shape and other structural features necessary in an organic inhibitor. See. e.g., Bjorkman P. J., Saper M. A., Samreoui, Bennett U. S., Strominger J. L., Wiley D. C., *Structure of the Human Class I Histocompatibility Antigen.* HLA-A2. Nature 1987; 439: 506–512. See also Bjorkman P. J., Saper M. A., Samraoui B., Bennett W. S., Strominger J. L., Wiley D. C., *The Foreign Antigen Binding Site and T Cell Recognition Regions of Class I Histocompatibility antigens.* Nature 1987; 329:512-518.

The metabolic control of the production of amylin from the islets of Langerhans can be determined as follows. Using the experimental protocols outlined in Example 1 below, and using a standard radioimmunoassay or immunometric assay developed for the measurement of amylin in biological fluids (see Yalow R. S., Berson 5A, J Clin Invest 1960; 39:1157), it will be possible to determine the metabolic variables which control the synthesis and release of amylin. So, for example, isolated islets can be incubated with a variety of concentrations of candidate molecules, both intermediary metabolites and signal molecules such as biologically active peptides, to determine which molecules exert a positive, and which a negative, effect on the synthesis and release of amylin. The response of the islets to the various signals can be determined by measurement of the synthesis and release of amylin into the medium in which the islets are incubated, and also by determining the rate of synthesis of amylin specific mRNA. One can then examine the effect of blocking molecules on this mechanism using the same techniques as outlined below for the amylin receptor itself.

Identification of the amylin receptor site will make it possible to provide for the direct blockage of its activity. In one embodiment of the invention, monoclonal antibodies which block insulin resistance are obtained by one of two methods. Using known techniques, following identification and, if desired, purification of the amylin receptor site, monoclonal antibodies against the receptor are raised. See, e.g., Roth R. A., Cassell D. J., Wong K. Y., Maddux B., Goldfine I. D., Monoclonal Antibodies to the Human Insulin Receptor Block Insulin Binding and Inhibit Insulin Action. Proc Natl Acad Sci USA 1982; 79:7312-7316.

Antibodies to the amylin receptor can be raised in BALB/c or other similar strains of mice by immunization with purified or partially purified preparations of amylin receptor, or with cells with a high concentration of amylin receptors. The spleens of these mice can be removed, and their lymphocytes fused to a mouse myeloma cell line. After screening of hybrids by known techniques, a stable hybrid will be isolated that produces antibodies against the amylin receptor. Such activity can be demonstrated by the ability of the antibody to prevent the binding of radiolabelled amylin (e.g., $^{125}$I-labelled amylin) to its receptor. The monoclonal antibody can then be examined for its ability to prevent the actions of amylin with respect to inhibition of glucose-induced insulin secretion in isolated islets and production of insulin resistance in skeletal muscle, as described in the examples below. More specifically, analysis of the monoclonal antibodies for prevention of the insulin resistance or insulin-release inhibitory actions of amylin can be performed utilizing the screening tests as outlined in Examples 1 and 2 below, substituting the monoclonal antibody for the substituted peptide in the experimental design as in Example 4 below.

A further approach involves the use of anti-idiotype antibodies. Anti-idiotype antibodies are raised against monoclonal antibodies directed against amylin such that the anti-idiotype will have complimentary binding affinity for the amylin receptor site without, of course, the activity promotion associated with amylin binding. Utilization of anti-idiotype antibodies for blocking viral binding to cells is known in the art. See, Kaufmann R. S., Noseworthy J. H., Nepom J. T., Finderg R., Fields B. N., Greene H. I., Cell Receptors for the Mammalian Reovirus. Monoclonal Anti-idiotypic Antibody Blocks Viral Binding to Cells. J Immunol 1983; 131:2539-2541. See also Burdette S. Schwartz R. S. Current Concepts:

Immunology-idiotypes and Idiotypic Networks. Med Int 1987; 317: 219–224.

Amylin activity can also be prevented by utilization of techniques involving bifunctional cross-linking agents. This technique allows for binding of the receptor by cross-linked amylin and/or amylin agonists with an agent so that amylin activity is prevented. By cross-linking such a labelled agent to, for example, amylin, CGRP, or biologically active subpeptides of either of them, using known techniques (see, e.g., Galardy et al., Photoaffinity Labelling of Peptide Hormone Binding Sites. J Biol Chem 1974; 249:3510–3518 and Yip C. C., Yeung C. W., Moule M. L., Photoaffinity Labelling of Insulin Receptor Proteins of Liver Plasma Membrane Preparations. Biochemistry 1980; 19:70–76 (cross-linking agent N-hydroxysuccinimide ester of p-azidobenzoic acid) they will prevent activity upon binding to the amylin receptor.

Chemical cross linkers, such as disuccinimidyl suberate, the N-hydroxysuccinimide ester of pazidobenzoic acid, or other similar chemical compounds will be covalently bound to amylin, or subpeptides of the amylin molecule, or other amylin agonists such as CGRP, by the appropriate standard methods as reported in the literature. The derivative will then be purified by chromatography on GM-cellulose, or another appropriate stationary phase, and the purity assessed by polyacrylamide gel electrophoresis or reverse phase chromatography on C-8 or C-18 columns, with a mobile phase of 0.1- or 1% trifluoroacetic acid and an acetonitrile gradient. The cross-linked molecule is bioassayed for its ability to inhibit the insulin-inhibitory and insulin-resistance producing effects of amylin, according to the experimental protocols outlined in the examples below. The cross-linked amylin will be assessed for its ability to bind to amylin receptors, for its immunoreactivity, and is labelled with $^{125}$I for example, to enable it to be used as a probe for the detection of the amylin receptor.

Another approach to the construction of suitable amylin competitive inhibitors involves biological screening for synthetic or other antagonists. Here, suitable competitive inhibitors are determined by in vitro experimentation, whereby a potential antagonist is added to isolated muscle or muscle cells and purified amylin, in the presence or absence of insulin, and glucose uptake by cells in the tissue culture are monitored. An increase in uptake in the presence of a potential antagonist will indicate the compound had the required inhibitory properties. This approach allows for relatively quick microtitre plate analysis of numbers of potential synthetic antagonists. Isolated islets of Langerhans or isolated islet B cells can also be used in a similar protocol in which increased insulin output is monitored instead.

Additionally, immunoassay screening can also be utilized, whereby synthetic or other antagonists which displace amylin or anti-idiotype antibodies from monoclonal antibodies immobilized in microliter wells will demonstrate that such antagonists should be evaluated under the biological screening parameters discussed above. The compound to be tested or the amylin or anti-idiotype antibodies may be labelled. Immunoassay screening can be utilized as a first phase screening technique for a variety of potential antagonists. These screening methods can include the use of one or more positive and/or negative controls.

For the purposes of this invention, the compounds and compositions of the invention may be administered by any means that permits the hypoglycemic agents to function and affects the ability of amylin, levels of which may be enhanced by those agents and which are enhanced in type 2 diabetes, to inhibit glucose-related actions of insulin. For example, administration may be orally, parenterally, by inhalation spray, or rectally in formulations containing conventional non-toxic pharmaceutically acceptable carriers, adjuvants and vehicles. The term parenteral as used herein includes subcutaneous intravenous, intramuscular, and intraarterial injections and infusion techniques. Intraarterial and intravenous injection as used herein includes administraton through catheters. It is prefered that the compounds and compositions of the invention are administered in an amount sufficient to maintain amylin function to within the range of normal. However, compositions within the scope of the invention include all compositions, whether or not they contain a hypoglycemic agent, wherein an amylin antagonist or antagonists are contained in an amount effective to achieve their intended purpose. When non-injection methods are used (e.g., oral administraton), use of time-release preparations to control the rate of release of the active ingredient is preferred.

Pharmaceutical compositions containing the active ingredient or ingredients may be in any form suitable for the intended method of administration, and may include suitable pharmaceutically acceptable carriers comprising excipients and auxiliaries which facilitate processing of the active compounds into preparations that can be used pharmaceutically. When used for oral use, for example, tablets, troches, lozenges, aqueous or oil suspensions, dispersible powders or granules, emulsions, hard or soft capsules, syrups or elixers may be prepared. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide a palatable preparation. Tablets containing the active ingredient or ingredients in admixture with non-toxic pharmaceutically acceptable excipients which are suitable for manufacture of tablets are acceptable. These excipients may be, for example, inert diluents, such as calcium carbonate, sodium carbonate, lactose, calcium phosphate or sodium phosphate; granulating and disintegrating agents, such as maize starch, or alginic acid; binding agents, such as starch, gelatin or acacia; and lubricating agents, such as magnesium stearate, stearic acid or talc. Tablets may be uncoated or may be coated by known techniques to delay disintegration and adsorption in the gastrointestinal tract and thereby provide a sustained action over a longer period. For example, a time delay material such as glyceryl monostearate or glyceryl distearate alone or with a wax may be employed.

Formulations for oral use may also be presented as hard gelatin capsules wherein the active ingredient or ingredients are mixed with an inert solid diluent, for example, calcium carbonate, calcium phosphate or kaolin, or as soft gelatin capsules wherein the active ingredient is mixed with water or an oil medium, such as peanut oil, liquid paraffin or olive oil.

Aqueous suspensions of the invention contain the active materials in admixture with excipients suitable for the manufacture of aqueous suspensions. Such excipients include suspending agents, such as sodium carboxymethylcellulose, methylcellulose, hydroxypropylmethylcellulose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethyleneoxitol, a condensation product of ethylene oxide with a partial ester derived from a fatty acid and a hexitol (e.g., polyoxyethylene sorbitol mono-oleate), or a condensation product of ethylene oxide with a partial ester derived from a fatty acid and a hexitol anhydride (e.g., polyoxyethylene sorbitan mono-oleate). The aqueous suspension may also contain one or more preservatives such as ethyl or n-propyl p-hydroxybenzoate, one or more coloring agents, one or more flavoring agents and one or more sweeting agents, such as sucrose or saccharin.

Oil suspensions may be formulated by suspending the active ingredient in a vegetable oil, such as arachis oil, olive oil, sesame oil or coconut oil, or in a mineral oil such as liquid paraffin. The oil suspension may contain a thickening agent, such as beeswax, hard paraffin or cetyl alcohol. Sweetening agents, such as those set forth above, and flavoring agents may be added to provide a palatable oral preparation. These compositions may be preserved by the addition of an antioxidant such as ascorbic acid.

Dispersible powders and granules of the invention suitable for preparation of an aqueous suspension by the addition of water provide the active ingredient or ingredients in admixture with a dispersing or wetting agent, a suspending agent, and one or more preservatives. Suitable dispersing or wetting agents and suspending agents are exemplified by those disclosed above. Additional excipients, for example sweetening, flavoring and coloring agents, may also be present.

The pharmaceutical compositions of the invention may also be in the form of oil-in water emulsions. The oily phase may be a vegetable oil, such as olive oil or arachis oil, a mineral oil, such as liquid paraffin, or a mixture of these. Suitable emulsifying agents include naturally-occurring gums, such as gum acacia and gum tragacanth, naturally occurring phosphatides, such as soybean lecithin, esters or partial esters derived from fatty acids and hexitol anhydrides, such as sobitan mono-oleate, and condensation products of these partial esters with ethylene oxide, such as polyoxethylene sorbitan mono-oleate. the emulsion may also contain sweetening and flavoring agents.

Syrups and elixirs may be formulated with sweetening agents, such as glycerol, sorbitor or sucrose. Such formulations may also contain a demulcent, a preservative, a flavoring or a coloring agent.

The pharmaceutical compositions of the invention may be in the form of an injectable preparation, such as a sterile injectable aqueous or oleaginous suspension. This suspension may be formulated according to the known art using suitable dispersing or wetting agents and suspending agents, such as those which have been mentioned above. The serial injectable preparation may also be a serial injectable solution or suspension made using a non-toxic parenterally-acceptable diluent or solvent, such as a solution in 1,3-butanediol. Among the acceptable vehicles and solvents that may be employed are water, Ringer's solution and isotonic sodium chloride solution. In addition, sterile fixed oils may conventionally be employed as a solvent or suspending medium. For this purpose any bland fixed oil may be employed including synthetic mono- or diglycerides. In addition, fatty acids such as oleic acid may likewise be used in the preparation of injectables.

The compounds of this invention may also be administered in the form of suppositories for rectal administraton of the drug. These compositions can be prepared by mixing the drug with a suitable non-irritating excipient which is solid at ordinary temperatures but liquid at the rectal temperature and will therefore melt in the rectum to release the drug. Such materials are coca butter and polyethylene glycols.

The amount of active ingredient or ingredients that may be combined with the carrier material to produce a single dosage form will vary depending upon the host treated and the particular mode of administration. For example, a time-release formulation intended for oral administration to humans may contain at least minimum amounts of active material compounded with an appropriate and convenient amount of carrier material which may vary from about 1 to about 95% of the total composition. It is preferred that pharmaceutical compositions be prepared which provide easily measurable amounts for administration.

It will be understood, however, that the specific dose level for any particular patient will depend on a variety of factors including the activity of the specific compound employed; the age, body weight, general health, sex and diet of the individual being treated; the time and route of administraton; the rate of excretion; other drugs which have previously been administered; kind of concurrent treatment, if any, and frequency of treatment; the nature of the effect desired; and the severity of the particular disease undergoing therapy, as is well understood by those skilled in the art.

The following Examples are set forth to assist in understanding the invention and should not, of course, be construed as specifically limiting the invention described and claimed herein. Such variations of the inventions which would be within the purview of those in the art, including the substitution of all equivalents now known or later developed, are to be considered to fall within the scope of the invention as hereinafter claimed.

EXAMPLE 1

These experiments illustrate the fact that native amylin and synthetic, unamidated amylin both reduce the rate of glycogen synthesis in both basal and insulin stimulated modes. The initial experiments were performed with amylin-peptide 1-37 which was synthesized according to the method of Baray and Merrifield, as outlined above, in which the disulfide bridge between Cys(2) and Cys(7) had been reformed.

After having been starved overnight, rats were sacrificed and soleus muscles strips were prepared as previously described. See Crettaz M., Prentki M., Zaninetti D., Jeanrenaud B., Insulin Resistance in Soleus Muscle from Obese Zucker Rats. Biochem J 1980; 186:525–534 and Espinal J., Dohm L., Newsholme E. A., Sensitivity to Insulin of Glycolysis and Glycogen Synthesis of Isolated Soleus Muscle Strips from Sedentary. Exercised and Exercise-trained Rats. Biochem J 1983; 212:453–458.

The isolated muscles were transferred immediately into siliconized 25 ml Erlenmeyer flasks containing Krebs-Ringer bicarbonate buffer at 37° C. with the following composition (in mM); NaCl (104), Hepes (6.7), $NaHCO_3$ (22), KCl (4), $CaCl_2$ (1.1), $KH_2PO_4$ (1), MgSO₄ (1), pyruvate (5), succinate (5), 1-glutamate (5), d-glucose (5.5). Defatted bovine serum albumin (See Chen R., Removal of Fatty Acids from Serum Albumin by Charcoal Treatment. J Biol Chem 1967; 242: 173–181) was added to a final concentration of 1.5% and the pH was adjusted to 7.31. The medium was gassed with $O_2/CO_2$ (95/5) during preparation; flasks were gassed with $O_2/CO_2$ continuously during the incubation. After 30 minutes preincubation the muscles were transferred into other flasks with identical Krebs-Ringer bicarbonate buffer with pyruvate, succinate or 1-glutamate, containing UDP-14C-glucose (0.5 μCi/ml) and various concentrations of insulin (1, 10, 100 and 100 mU/L). Amylin was added to half the experiments to give a final concentration of 120 nmol/L. After 60 minutes incubation the muscles were quickly removed, blotted and freeze-clamped in liquid $N_2$ and processed for determination of the extent of UDP-$^{14}$C-glucose incorporation into glycogen. See Guendet Q., Loten E., Jenrennud B., Renold A., Decreased Basal Non-insulin Stimulated Glucose Uptake and Metabolism by Skeletal Soleus Muscle Isolated from Obese-hyberglycasmic Mice. J. Clin. Invest. 1979; 58:1078–1088. The effects of insulin on glucose transport were determined by measurement of rates of conversion of glucose to lactate. See Leighton B., Challis R. A. J., Lozeman F. J., Newsholme E. A., Effects of Dexamethasone on Insulin-stimulated Rates of Glycolysis and Glycogen Synthesis in Isolated Incubated Skeletal Muscles of the Rat. Biochem J 1987; 246:551–554 and Engel P., Jones J., Causes and Elimination of Erratic Blanks in Enzymatic Metabolite Assays Involving the Use of NAD+ in Alkaline Hydrazine Buffers. Anal Biochem 1978; 88:475–484.

The results are set out in the accompanying TABLE 1, showing the rate of glycogen synthesis (measured a the rate of incorporation of $^{14}$C-UDP-glucose into glycogen) against insulin concentration in the presence and absence of amylin. The experiments were performed in the presence of 120 nanomoles per liter of amylin. Each result at 1 and 100 microunits per mL of insulin concentration is the mean of 11 replicate experiments. Each result at 10 and 1000 microunits per mL is the mean of 5 replicates.

The results demonstrate that at all physiological concentrations of insulin (from 1 to 100 microunits per mL), glycogen synthesis is slowed in the presence of amylin. The differences are statistically significant (p is less than 0.05 at 1 and 100 microunits per mL by the Mann-Whitney U test).

It will be observed that the inhibition of glycogen synthesis by amylin persists at low, and presumably even zero, insulin concentrations. Amylin therefore has its own action, which is contrary to that of insulin but probably not mediated by direct antagonism of insulin action. In support of this, we have observed that amylin is not capable of significantly displacing insulin from its receptor on red blood cells. This evidences the existence of a receptor for the peptide amylin in the skeletal muscle cells of the rat. Of course, this experiment was performed with amylin synthesized according to the human sequence and it is likely, although as yet unknown, that the sequence of "rat-amylin" is distinct from that of human amylin. Therefore, it is also likely that the effect of rat amylin in this system could be significantly greater than that of human amylin.

Isolated native amylin also has the biological effect of inhibiting the rates of basal and insulin-stimulated glycogen synthesis in skeletal muscle, as the following experiments demonstrate. Experiments were performed with human amylin, isolated and characterized from the pancreas of a human Type 2 diabetic according to the method of Cooper G. J. S. et al., Proc Natl Acad Sci 1987; 84:8628–8632. Samples used were from the broad peak area of the final isolation step of HPLC reverse phase chromatography with a mobile phase of 1.0 percent trifluoroacetic acid, with gradient elution by acetonitrile from 5 to 80 percent over 45 minutes, on a C-18 column with detection of peptides by ultraviolet spectrophotometry at 280 nm. The exact concentration of amylin was confirmed by quantitative amino acid analysis and by the yield on amino acid sequencing. A graph can be constructed showing the elution profile of amylin, with the Yaxis representing an $AUFS_{280}$ of 0.02 or 0.05 absorbance units (full scale deflection) and the X-axis the percentage acetonitrile in the gradient. Amylin eluted at an acetonitrile percentage of 67.9 percent.

The experiments were performed in the manner indicated in Example 4 below, except that amylin isolated from a human diabetic pancreas was used in place of material synthesized chemically. Samples indicated as "amylin" contained native amylin at the stated concentrations, as well as insulin at a basal concentration of 10 μU/mL (TABLE 2), or at the stimulatory level of 100 μU/mL (TABLE 3). These results are presented below in TABLES 2 and 3, where n represents the number of replicates in each group. The rates of glycolysis, as indicated by the rates of lactate synthesis, were not significantly different between groups. Statistical analysis was performed by the t-test, and significance was

TABLE 1

Dose Response: Amylin vs. Glycogen Synthesis Inhibition.
EFFECT OF SYNTHETIC AMYLIN AT
VARIOUS INSULIN CONCENTRATIONS.
(Constant Amylin Concentration: 120 nmol/L).

| INSULIN CONCENTRATION (μU/ml) | Repl. | GLYCOGEN SYNTHESIS (μmol/h/g)* | | | | RELATIVE GLYCOGEN SYNTHESIS INHIBITION |
|---|---|---|---|---|---|---|
| | | CONTROL ONLY | | AMYLIN ADDED | | |
| | | Mean | Error | Mean | Error | |
| 1 | 11 | 2.09 | 0.18 | 1.54 | 0.18 | 26% |
| 10 | 5 | 2.25 | 0.52 | 1.72 | 0.21 | 24% |
| 100 | 11 | 5.32 | 0.26 | 4.33 | 0.28 | 19% |
| 1000 | 5 | 4.10 | 0.72 | 4.50 | 0.36 | — |

*micromoles glucosyl units per hour gram wet muscle tissue. RELATIVE GLYCOGEN SYNTHESIS INHIBITION equals the percentage by which glycogen synthesis is reduced from control STANDARD ERROR of the mean is defined as the standard deviation divided by the square root of the number of replicates.

assessed as the difference between an amylin treated sample and the appropriate insulin-treated control.

TABLE 2

Glycogen Synthesis Inhibition in Rat Muscle Cells
EFFECT OF NATURAL WHOLE AMYLIN AT
BASAL INSULIN CONCENTRATION
(Insulin Concentration: 10 isU/ml)

| AMYLIN CONCEN-TRATION | | GLYCOGEN SYNTHESIS ($\mu$mol/h/g)* | | RELATIVE INSULIN RESISTANCE |
|---|---|---|---|---|
| (nmol/L) | Repl. | Mean Value | Std Error | |
| None (Control) | — | 4 | 1.43 | 0.10 | 0% |
| Amylin, Fraction 2 | 0.4 | 4 | 1.12 | 0.06 | 22% |
| Amylin, Fraction 3 | 0.4 | 3 | | | |
| Average | | | 1.12 | 0.06 | 22% |
| Amylin, Fraction 2 | 2.0 | 4 | 0.82 | 0.12 | 43% |
| Amylin, Fraction 3 | 2.0 | 4 | | | |
| Average | | | 0.72 | 0.12 | 50% |

*micromoles glycosyl units per hour per gram wet muscle tissue. RELATIVE GLYCOGEN SYNTHESIS INHIBITION equals the percentage by which glycogen synthesis is reduced from control. STANDARD ERROR of the mean is defined at the standard deviation divided by the square root of the number of replicates. All measurements of glycogen synthesis were determined by the T-test to be significantly different from the control value with $p < 0.025$ in all cases.

TABLE 3

Glycogen Synthesis Inhibition in Rat Muscle Cells
EFFECT OF NATURAL WHOLE AMYLIN AT
STIMULATORY INSULIN CONCENTRATION
(Insulin Concentration: 100 $\mu$U/ml)

| AMYLIN CONCEN-TRATION | | GLYCOGEN SYNTHESIS ($\mu$mol/h/g)* | | RELATIVE INSULIN RESISTANCE |
|---|---|---|---|---|
| (nmol/L) | Repl. | Mean Value | Std Error | |
| Experiment #1 | | | | | |
| None (Control) | — | 3 | 2.83 | 0.10 | 0% |
| Amylin Fraction 2 | 0.4 | 4 | 2.00 | 0.29 | 29% |
| Experiment #2 | | | | | |
| None (Control) | — | 4 | 3.69 | 0.57 | 0% |
| Amylin Fraction 2 | 2.0 | 5 | 1.97 | 0.45 | 47% |

*Table 2 for explanation.

It can be seen that concentrations of extracted amylin as low as 0.4 nmol/L are effective in significantly reducing the rate of both basal and insulin stimulated glycogen synthesis in isolated rat muscle, and that an amylin concentration of 2.0 nmol/L reduces the basal rate of glycogen synthesis by 50 percent, and the insulin-stimulated rate by 47 percent. This must be contrasted with the results of the previous experiment performed in an identical manner but with chemically synthesized amylin, in which a concentration of unamidated synthetic amylin of 120 nmol/L was required to produce a significant reduction in glycogen synthesis.

These results demonstrate that amylin extracted from a natural source was more potent than amylin that was chemically synthesized as described, by at least a factor of 120/2, or 60 fold. This indicates that there is a feature of the isolated molecule that is not completely reproduced by synthesized material. This may be because the reformation of the Cys(2)-Cys(7) disulfide bridge is incomplete in the synthetic molecule.

EXAMPLE 2

Experiments with synthetic subpeptides of amylin were also performed, the individual structures of which have already been indicated in the text of the application, as subpeptides [3]-[5]. Amylin subpeptides used in experiments accomplished by the above methods to localize the glycogen-synthesis inhibitory active site of amylin included: [3] Amylin 1-16, with the Cys(-2)-Cys(7) bridge reformed; [4] Amylin 1-16, reduced; [5] Amylin 8-37; [6] Amylin 27-37; and [7] Amylin 1-16 with Ser residues substituted for the Cys residues 2 and 7.

All peptides were synthesized on an Applied Biosystems 430A Peptide Synthesizer, using commercially available Pam resins and t-butyloxycarbonyl protected amino acids and reagents, with cleavage of the peptide from the resin and the side-chain protecting groups simultaneously by anhydrous hydrofluoric acid treatment with anisole as a free radical trap, followed by extraction of side-chain protecting groups with ether, dissolution of the peptide in 15 percent acetic acid, filtration from resin and Purification by HPLC on a C-8 reverse phase column (Aquapore RP-3000, Brownlee Laboratories, Santa Clara, Calif.) with a mobile phase of 0.1% aqueous trifluoro-acetic acid on an acetonitrile gradient and detection of peptides by ultraviolet spectrophotometry at 206 nm. The disulfide bridge linking the cysteine residues at positions 2 and 7 of peptide [3] was reformed by the following method. After synthesis, the peptide was dissolved in dilute solution in water at pH 8.0 for 12 hours, and was then recovered by lyophilization and repurified on a High Performance Liquid Chromatography (HPLC) system by reverse phase chromatography in an acetonitrile - aqueous 0.1% trifluoroacetic acid system with detection of peptides by ultraviolet absorbance at 206 nm. See, e.g., Cooper G. J. S. et al., Proc. Natl Acad. Sci. USA 1987; 84:8626-8632. The disulfide bond of peptide [4] was retained in a reduced form by reduction with dithiothreitol after the de-blocking procedure following synthesis.

The results indicated that significant activity was present in the subpeptides [3], [4] and [5], i.e., amylin 1-16 with Cys (2)-Cys (7) reformed by oxidation, amylin 1-16 reduced, and amylin 8-37 (data not shown). Activity was absent from the subpeptides [6] and [7], i.e., from amylin 27-37 and amylin 1-16 with serine residues substituted for cysteine residues. Accordingly, the activity of amylin in inhibiting the rates of both basal and insulin-stimulated glycogen synthesis in skeletal muscle are dependent on certain features of the amylin molecule:

1. The presence of the cys residues at positions 2 and 7 in the molecule;
2. Other portions of the sequence between residues 7 and 16.

EXAMPLE 3

Experiments using amylin 1-16 with serines substituted for cysteines at positions 2 and 7 (ser$^2$, ser$^7$ amylin 1-16) as an amylin blocker were performed as described in Example 2. We utilized an artificially synthesized peptide amylin 1-16, with serines substituted for cysteines and extracted human amylin. Experiments were performed with amylin concentrations of both 2.0 and 0.2 nmoll/L, a stimulatory insulin concentration of 100 uU/mL, and with the ser$^2$, ser$^7$ amylin 1-16 at a concentration of $10.^{-5}$ mol/L. The results obtained in these experiments are included in the following TABLE 4.

TABLE 4

Amylin Antagonist Reduction of Glycogen Synthesis Inhibition
EFFECT OF MODIFIED AMYLIN SUBPEPTIDE $SER^2$, $SER^7$
AMYLIN 1-16 IN RAT MUSCLE CELLS
(Stimulatory Insulin Concentration: 100 KU/ml).

| CONCENTRATION (nmol/ml) | | | GLYCOGEN SYNTHESIS ($\mu$mol/h/g)* | | Rltv Insulin | Rltv Antg |
| --- | --- | --- | --- | --- | --- | --- |
| AMYLIN | ANTG | Repl. | Mean Value | Std. Error | Resist | Effect |
| Experiment #1 | | | | | | |
| None (Control) | 0.0 | 0 | 3 | 2.83 | 0.10 | 0% | — |
| Amylin alone | 0.2 | 0 | 4 | 2.00 | 0.29 | 29% | 0% |
| Amylin & Antgnst | 0.2 | 10,000 | 3 | 2.22 | 0.72 | 22% | 24% |
| Experiment #2 | | | | | | |
| None (Control) | 0.0 | 0 | 3 | 3.69 | 0.57 | | 0% |
| Amylin alone | 2.0 | 0 | 3 | 1.97 | 0.45 | 47% | 0% |
| Amylin & Antgnst | 2.0 | 10,000 | 3 | 2.63 | 0.29 | 20% | 38% |

*micromoles glycosyl units per hour per gram wet muscle tissue. RELATIVE GLYCOGEN SYNTHESIS INHIBITION equals the percentage by which glycogen synthesis is reduced from control. RELATIVE ANTAGONIST EFFECT equals the percentage by which relative insulin resistance is reduced from amylin alone. STANDARD ERROR of the mean is defined as the standard deviation divided by the square root of the number of replicates.

These results demonstrate that the amylin used at concentrations of both 2.0 nmol/L and 0.2 nmol/L was active in the inhibition of glycogen synthesis, with a significant decrease over controls in both experiments. On the other hand, after the addition of ser2, ser7 amylin 1-16 there was no significant difference between the insulin stimulated rates of glycogen synthesis, and that in the samples with insulin, amylin and $ser^2$, $ser^7$ amylin 1$\neq$16 treated muscle. Although the inhibitory effect of the $ser^2$, $ser^7$ amylin 1-16 is incomplete, it can be seen that the rate of glycogen synthesis moved back toward the uninhibited rate in both experiments at the two concentrations of amylin (2.0 and 0.2 nmol/L).

Thus, a competitive inhibitor of the action of amylin, in this case $ser^2$, $ser^7$ amylin 1-16 (of the type in which different amino acids are substituted for important residues within the active site of a peptide), is capable of partially ameliorating the insulin resistance produced by amylin alone. Additionally, the substituted peptide $ser^2$, $ser^7$ amylin 1-16 is an inhibitor, we believe a competitive inhibitor, of the effect of amylin to inhibit the rate of insulin-stimulated glycogen synthesis in isolated skeletal muscle.

EXAMPLE 4

The following experiments illustrate the fact that subpeptides of amylin can act to reduce the amount of insulin produced by isolated islets of Langerhans in response to a standard glucose challenge. Similar results have been obtained using whole amylin. All experiments were performed by known methods used in experimental practice. See, e.g., Lacey P. E., and Kostianovsky M., Method for the Isolation of Intact Islets of Lanaerhans from the Rat Pancreas. Diabetes 1967; 16:35-39.

Briefly, rats were killed, and islets of Langerhans were isolated from their pancreases. Experiments were performed either with freshly isolated islets or after overnight incubation of islets (23 h) in standard culture medium and conditions at 37° C. Synthetic amylin peptide 27-37 or synthetic calcitonin gene related peptide (CGRP) was dissolved in a 1.0 mmol/L citric acid/sodium citrate buffer, pH 3.0, and the concentration of the amylin 27-37 was verified by quantitative amino acid analysis. See, e.g., Cooper G. J. S. et al., Proc Natl Acad Sci USA 1987; 84:8628-8632. Incubation of islets for these experiments was carried out in standard Krebs-Heinsleit buffer, and it was verified that the addition of the 1.0 mmol/L citrate buffer had no effect on the pH of the incubation medium. Stimulation of islets was carried out at the standard stimulatory glucose concentration of 10 mmol/L.

Production of insulin is expressed as $\mu$U/islet/h. All experiments were performed with five replicates per point. The integrity of the islet response was assessed by comparing the responses after stimulation of different aliquots of islets by two and ten mmol/L glucose, respectively, and the strength of the inhibitory response was judged against that induced by 1 $\mu$g/ml (650 nmol/L) somatostatin. Somatostatin is a 14 amino acid peptide which is a known, potent inhibitor of the insulin secretory response of islet B-cells to glucose. Arimura A. Biomed res1981; 2:233-257. CGRP has also been shown to be a potent inhibitor of glucose stimulated insulin secretion. Petterson M., Ahren B., Bottcher G., Sundler F., Endocrinology 1986; 119:865-869.

The results are shown in TABLE 5 below and all results are expressed as standard error of the mean (s.e.m.). The significance of differences between the means of groups is assessed by the t-test. The result of stimulation by 10 mmol/L glucose is compared with the results of stimulation at 2 mmol/L glucose. In all other experimental conditions, the significance of the inhibitory effect is measured against the effect of 10 mmol/L glucose alone.

TABLE 5

INSULIN SECRETION IN RAT ISLET CELLS.
Effect of Synthetic Partial Amylin and Other Hormones.
(Stimulatory Glucose Level: 10 mmol/L).

| SUBSTANCE INHIBITION | CONCENTRATION (nmol/L) | Repl. | GLYCOGEN PRODUCTION ($\mu$U/islet/hr) Mean Value | Std. Error | RELATIVE INSULIN SECRETION |
| --- | --- | --- | --- | --- | --- |
| None (Control) | — | 5 | 80 | 14 | 0% |
| Amylin 27-37 | 1000 | 5 | 65 | 17 | 19% |
| Amylin 27-37 | 100 | 5 | 48 | 9 | 40% |
| Amylin 27-37 | 10 | 5 | 45 | 7 | 44% |
| Somatostatin | 650 | 5 | 44 | 12 | 45% |
| CGRP 27-37 | 1000 | 5 | 46 | 10 | 42% |

TABLE 5-continued
INSULIN SECRETION IN RAT ISLET CELLS.
Effect of Synthetic Partial Amylin and Other Hormones.
(Stimulatory Glucose Level: 10 mmol/L).

| SUB-STANCE INHIBITION | CONCENTRATION (nmol/L) | Repl. | GLYCOGEN PRODUCTION ($\mu$U/islet/hr) Mean Value | Std. Error | RELATIVE INSULIN SECRETION |
|---|---|---|---|---|---|
| CGRP 27-37 | 100 | 5 | 36 | 8 | 55% |
| CGRP 27-37 | 10 | 5 | 36 | 9 | 55% |

RELATIVE INSULIN SUPPRESSION equals the percentage by which insulin production is reduced from control. "CGRP" Calcitonin Gene Related Peptide. STANDARD ERROR of the mean is defined as the standard deviation divided by the square root of the number of replicates.

These experiments indicate that the peptide amylin 27-37 is a potent inhibitor of glucose stimulated insulin secretion from the isolated rat islet. There was no significant difference between the inhibition of insulin secretion seen with various concentrations of amylin 27-37 and that seen with somatostatin (1 ug/mL; 650 nmol/L), a known potent inhibitor of insulin secretion, or with the varying concentrations of the peptide CGRP 27-37. There was a trend for the inhibition caused by CGRP 27-37 to be slightly greater than that caused by amylin 27-37, but this never reached significance.

As an insufficient insulin response to glucose is one of the characteristic pathophysiological features of Type 2 diabetes, and as there is likely to be an excessive production of amylin in that state (as shown by the presence of large amounts of amyloid), this action of amylin may very well be diabetogenic (tending to cause diabetes).

Utilizing the information provided in Example 3 above, one or more amylin peptides with substitutions of amino acids in the sequence of amylin 27-37 can be produced as an inhibitor of the effect of amylin 27-37 in inhibiting the insulin response to a glucose stimulus. Such a substituted peptide, and other compounds with similar properties, will be of great benefit in treatment of Type 2 diabetes mellitus.

EXAMPLE 5

We have also shown that amylin acutely produces diabetes (fasting hyperglycemia greater than 140 mg/dL) when administered intravenously. Eight normal rats were injected with a 100 $\mu$g bolus of amylin (rat amylin, Bachem, Torrance, Calif.). An intravenous amylin bolus produced a profound hyperglycemia to diabetic levels within 15-30 minutes (usually around 200 mg/dL). This hyperglycemia persists for several hours. The hyperglycemia is partly accounted for by an increase in hepatic (endogenous) glucose output and partly by an increased impediment in peripheral glucose disposal. It causes a transient increase in plasma lactate, believed to be because of increased glycolytic flux or through glycogenolysis in muscle and liver. There is an increase in respiratory quotient (RQ) after amylin only when somatostatin is absent and insulin is allowed to increase in response to hyperglycemia. During somatostatin infusion (no endogenous insulin release), there is no change in RQ, indicating no change from lipid to carbohydrate fuel usage in response to amylin in the fasted animal.

EXAMPLE 6

In this experiment we have shown that the amylin agonist CGRP8-37 also functions to partly antagonize amylin action. Insulin was obtained as Humulin-R, 100U/mL, recombinant human insulin (Eli Lilly, Indianapolis, Ind.). Amylin, obtained as rat amylin (Bachem, Torrance, Calif.) and 8-37 human CGRP (Bachem, Torrance Calif.) were also used. An antagonist assay was performed in vitro using the isolated soleus muscle from rats. It measured the rate of incorporation of radiolabelled glucose into muscle glycogen as follows: (1) under hormone-free conditions (zero insulin, zero amylin, zero hCGRP$_{8-37}$ (antagonist)); (2) under conditions of stimulation of glycogen formation with insulin (1000 $\mu$U/mL insulin, zero amylin, zero antagonist); (3) under conditions where the near maximal stimulation of glycogen formation has been inhibited with amylin (1000 $\mu$U/mL insulin, 20 nM amylin, zero antagonist); and, (4) under conditions where the suppression of glycogen formation by amylin has been disinhibited by an antagonist to the amylin action (1000 $\mu$U/mL insulin, 20 nM amylin), range of concentrations of antagonist (0, 1 nM, 10 nM, 100 nM, 300 nM, 1 $\mu$M, 10 $\mu$M). There were therefore 9 treatment groups (conditions 1,2,3 and six subgroups of condition 4).

The right and left soleus muscles of 4-hour fasted rats were removed immediately after decapitation of the animals, divided in half and temporarily placed in physiological saline. Muscles were assigned to different treatment groups so that the 4 muscle pieces from each animal were evenly distributed among the 9 flasks representing the different assay conditions. Each flask contained 4 muscle pieces (replicates) bathed in 10 mL of Krebs-Ringer buffer+5.5 mM glucose, equilibrated with 95% $O_2$ and 5% $CO_2$ at 37° C. by passing a gas stream of this mixture over the surface of the continuously agitated warmed liquid. Pharmacologically active agents were added to the 10mL of medium to result in the above stated concentrations and mixtures. After a 30 minute "preincubation" period, 0.5 $\mu$Ci of U-$^{14}$C-glucose was added to each flask and incubated for a further 60 minutes. Each muscle piece was then rapidly removed, blotted and frozen in liquid $N_2$, weighed and stored for subsequent determination of $^{14}$C-glycogen.

Frozen muscle specimens were digested in 1 mL 60% potassium hydroxide at 70° C. for 45 minutes. Dissolved glycogen was precipitated out by addition of 3mL absolute ethanol and cooling to −20° C. overnight. The supernatant was aspirated and the glycogen washed with ethanol, aspirated and dried under vacuum. The remaining glycogen was redissolved in water and scintillation fluid and counted for $^{14}$C.

From a knowledge of the specific activity of $^{14}$C-glucose in the 5.5 mM glucose of the incubation medium, and the total $^{14}$C counts remaining in the glycogen extracted from each muscle, the net rate of glycogen synthesis over the final 60 minute incubation period was determined. This was normalized per mass of muscle and expressed as $\mu$moles of glucosyl units incorporated into glycogen per hour per gram of muscle. The antagonist dose/response curve was fitted to a 4-parameter logistic model using a least-squares iterative routine (ALLFIT, v2.7, NIH, MD) to derive the $EC_{50}$ for disinhibition.

Results showed a 3.7 fold increase in rate of glycogen synthesis upon addition of 1000 $\mu$U/mL insulin to the media. This was decreased approximately 83% by the addition of 20 nM amylin to below the basal level (0 amylin/ 0 insulin). From this inhibited level, there was a dose-dependent return in the rate of glycogen synthesis with addition of CGRP$_{8-37}$ to the incubation media.

As shown in FIG. 1, the increment in the rate of glycogen synthesis was up to about 115% of basal and was half maximal at a $CGRP_{8-37}$ concentration of 1.2 nM. Thus, the peptide $CGRP_{8-37}$ partly reverses the inhibitory effect of amylin on insulin-stimulated muscle glycogen synthesis and may be regarded as an amylin antagonist. The numbers beneath columns 3 to 9 indicate the measured $CGRP_{8-37}$ concentrations added, in the presence in each case of 20 nM amylin and 1000 μU/ml insulin.

EXAMPLE 7

This example shows the effect of the sulfonylurea hypoglycemic agents on amylin levels, as well as the effect on amylin levels of metformin, a biguanide hypoglycemic agent. HIT T-15 cells (HIT cells; American Type Tissue Collection, Rockville, MD; R. F. Santerre, et al. (1981) Proc. Nat. Acad. Sci. USA 78, 4339–4343.) were subcultured weekly in Ham's F-12 medium (Irvine Scientific, Santa Ana, Calif.) containing 10% horse serum (Gemini Bioproducts, Calabasas, Calif.), 2.5% fetal bovine serum (FBS; Gemini), 2 mM L-glutamine, and 10.0 mM glucose. Cells were maintained at 37° C. and 5% $CO_2$/ 95% humidified air and medium was replaced every 2 to 3 days. All experiments were performed with cells from passages 66 to 71.

Amylin and insulin secretion were measured using reagents of analytical grade unless otherwise indicated. The secretion medium was a Krebs-Ringer buffer (KRB) containing 119 mM NaCl, 4.74 mM KCl, 2,54 mM $CaCl_2$, 1.19 mM $MgSO_4$, 1.19 mM $KH_2PO_4$, 25 mM $NaHCO_3$, 10 mM HEPES and 0.1% protease-free bovine serum albumin (Cohn fraction V; Sigma Chemical Co., St. Louis Mo.) at pH 7.4. Glibenclamide (Sigma) was initially dissolved in ethanol (50 mg/ml) then diluted to working concentrations in KRB. The concentration of ethanol in test solutions was less than 0.01% (v/v) and did not affect the glucose-induced secretory response or cell viability as determined by trypan blue exclusion. Tolbutamide (Sigma) was initially dissolved in dimethylsulfoxide (50 mg/ml). DMSO concentrations in test solutions were less than 0.03% (v/v) and did not affect the secretory response. Metformin (Sigma) was diluted in KRB.

Five days before each secretion study cells were subcultured at $0.26 \times 10^6$ cells/0.8 ml medium/well in 24-well tissue culture plates (Corning Glass Works, Corning N.Y.). Medium was replaced on day 3. On day 5 cells were washed twice with 1.0 ml KRB then incubated in 1.0 ml KRB (30 minutes, 37° C.) in equilibrium with air. Cells were washed twice more prior to addition of 0.5 ml KRB containing the indicated concentrations of glucose, metformin, tolbutamide and glibenclamide. After a 60 minute incubation with test substance or substances, supernatants were centrifuged (5 minutes, 500×g, 5° C.; GPKR centrifuge, Beckman Instruments, Inc., Palo Alto, Calif.) to remove cell debris, then stored in polypropylene micro test tubes (Brinkman Instrument Co., Westbury, N.Y.) at −20° C. until analyzed by radioimmunoassay. Supernatants were analyzed for insulin and amylin content within one week of collection. Three wells per plate were randomly selected for cell quantitation. Cells were incubated with 75 μg trypsin and 30 μg EDTA in 150 μl normal saline (8 minutes, 37° C.), then counted on a Coulter Counter (Model Zf, Coulter Electronics, Hialeah, Fla.).

Immunoreactive insulin content in supernatants was measured using a commercial radioimmunoassay (IM.78; Amersham, Arlington Heights, Ill.). Hamster insulin in supernatant codiluted with human standards in the range 0.50 to 1.70 pmoles/ml. The radioimmunoassay for immunoreactive amylin was as follows. Assay diluent was phosphate-buffered saline (PBS; 137 mM NaCl, 2.68 mM KCl, 1.47 mM $KH_2PO_4$, 6.65 mM $Na_2HPO_4$) containing 0.1% Triton-X 100 (v/v), 0.01% $NaN_3$ (w/v), and 0.1% gelatin (v/v; teleostean, 45% aqueous solution, Sigma) at pH 7.4. All incubations were performed at 4° C. $^{125}$I-[Tyr 37]-human synthetic amylin tracer was iodinated by the chloramine-T method and purified on a C18 Sep-Pak (Waters Associates, Milford, Mass.). Specific activity was approximately 500 μCi/μg.

One hundred μl of human synthetic amylin standard (50 to 1200 pg/ml KRB; Bachem, Inc., Torrance, Calif.) or unknown sample was combined with 100 μl polyclonal rabbit antiserum specific for amylin (1:20,000, Peninsula Laboratories, Inc., Belmont, Calif.); no detectable cross-reactivity with human insulin, glucagon, somatostatin, pancreatic polypeptide or calcitonin gene-related peptide II; cross-reactivity ≦0.1% with rat calcitonin gene-related peptide I) in 12×75 mm polystyrene tubes (Sarstedt, Hayward, Calif.). Standards and unknowns were run in triplicate or duplicate respectively. After an 18 hour incubation, 100 μl of tracer containing 20,000 dpm was added and samples were incubated an additional 18 hours. To ensure complete immunoprecipitation of amylin:antibody complexes, 100 μl of rabbit gamma globulin (0.35 mg/ml, Scantibodies Laboratory, Santee, Calif.) and 100 μl of goat anti-rabbit gamma globulin (0.50 mg/ml, purified grade; Scantibodies) were added. After a 15 minute incubation, 1.0 ml 2% polyethylene glycol (w/v. MW 8,000; Sigma) in assay buffer was added and samples were centrifuged (30 minutes, 1500×g, 5° C.). Samples were decanted and pellets were counted on a gamma counter (model 1277; LKB Wallac, Turku, Finland).

Figure 2:
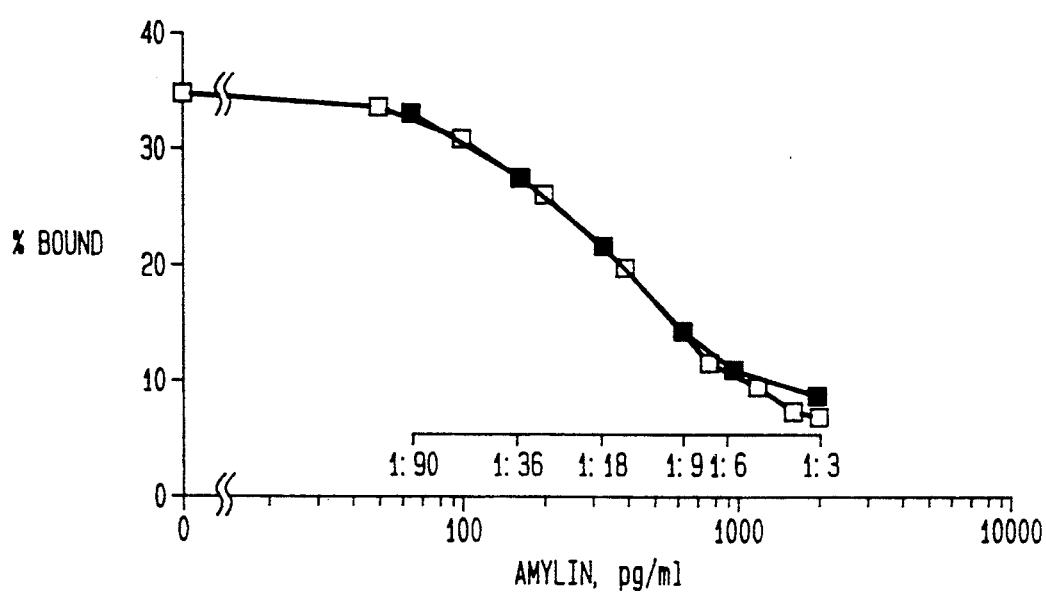
FIG. 2 shows the results of an amylin radioimmunoassay wherein the displacement of $^{125}$I-human amylin by increasing amounts of human amylin (solid square) and hamster amylin (open square) are shown. Each point represents the mean of triplicate (human) or duplicate (hamster) determinations.

FIG. 2 shows a typical standard curve for the displacement of $^{125}$I-[Tyr 37]-human amylin by unlabeled human amylin. The amylin radioimmunoassay had a sensitivity of 8 pg amylin/ml and linear range of 200 to 800 pg/ml. Hamster amylin codiluted with human amylin in the linear range. Recovery of human amylin added to HIT cell supernatants was 100±15% within this range. Glibenclamide (1 μM), metformin (100 μM), and tolbutamide (100 μM) had no effect on the displacement curve.

Figure 3A:
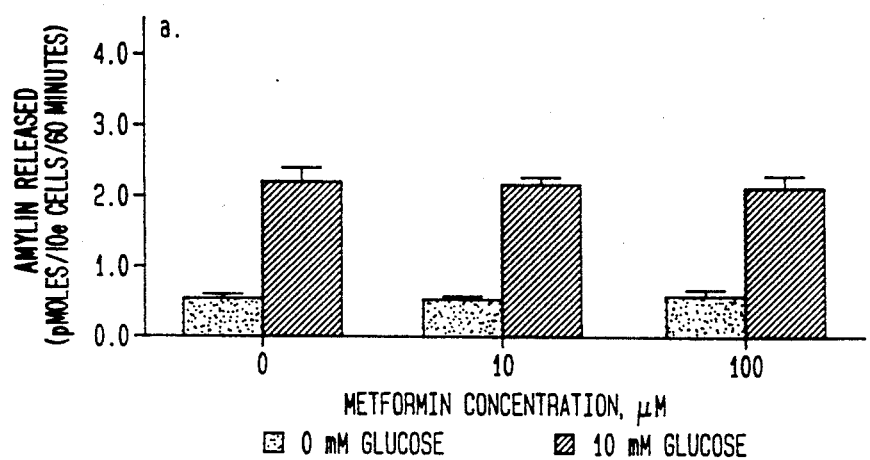
FIG. 3A-C shows the effects of metformin, tolbutamide and glyburide on basal and glucose-stimulated insulin release from HIT cells.
Figure 3B:
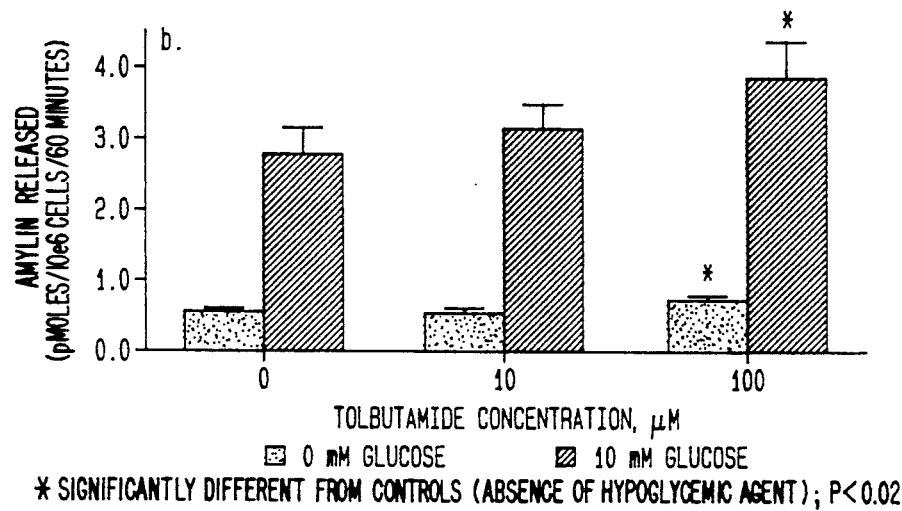
Figure 3C:
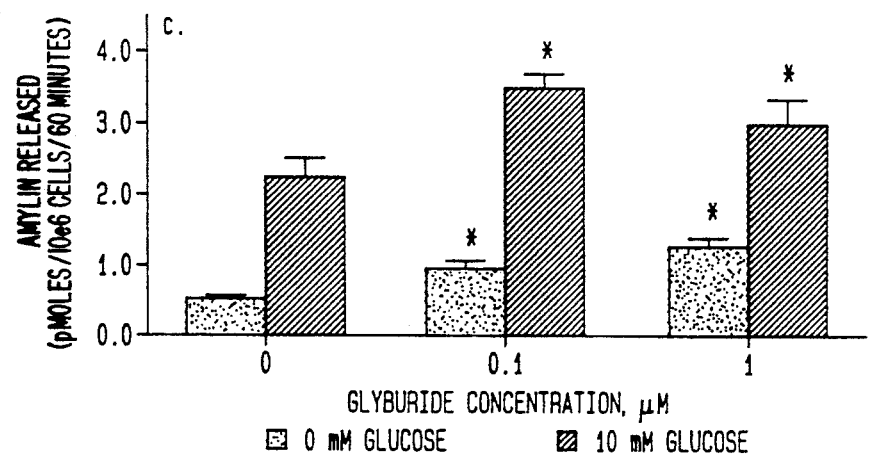
Figure 4A:
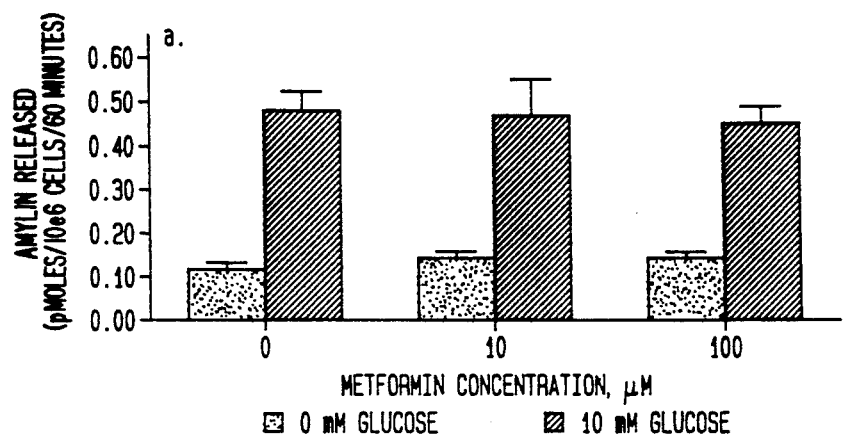
FIG. 4A-C shows the effects of metformin, tolbutamide and glyburide on basal and glucose-stimulated amylin release from HIT cells.

Data in FIGS. 3 and 4 are shown as the mean±S.D. of 4 replicate samples. An unpaired Student's t-test was used to compare secretion in the absence and presence of hypoglycemic agent (Statview 512+ program; Brain Power, Inc., Calabasas, Calif.).

FIG. 3 shows the effects of metformin, tolbutamide, and glibenclamide (also sometimes known as "glyburide") each at two concentrations, on insulin release from HIT cells at 0-glucose (basal release) and at 10 mM glucose (glucose stimulated secretion). In each experiment, under control (no drug) conditions, 10 mM of glucose evoked a 4 to 5-fold increase in insulin secretion, demonstrating the glucose responsiveness typical of pancreatic insulin secretion. FIG. 3a shows that at 10 and 100 μM metformin, within the therapeutic plasma concentration range (Klip, A. and Lieter, L. A. 1990 Diabetes 13:696–704) had no measurable effect on insulin secretion. By contrast, tolbutamide at 100 μM and glibenclamide at 0.1 and 1.0 μM significantly enhanced both basal and glucose-stimulated secretion of insulin.

The proportional increase was greater for basal release, more than two-fold for glibenclamide, while the absolute increase was greater for glucose stimulated release. Glibenclamide had effects at much lower concentrations than did tolbutamide, in line with the much higher doses required for tolbutamide compared with glibenclamide in the treatment of patients with NIDDM.

Figure 4B:
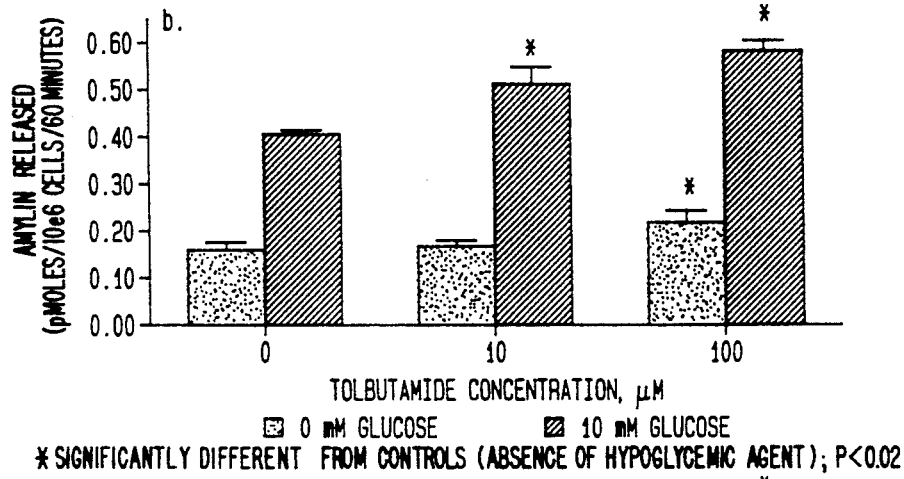
Figure 4C:
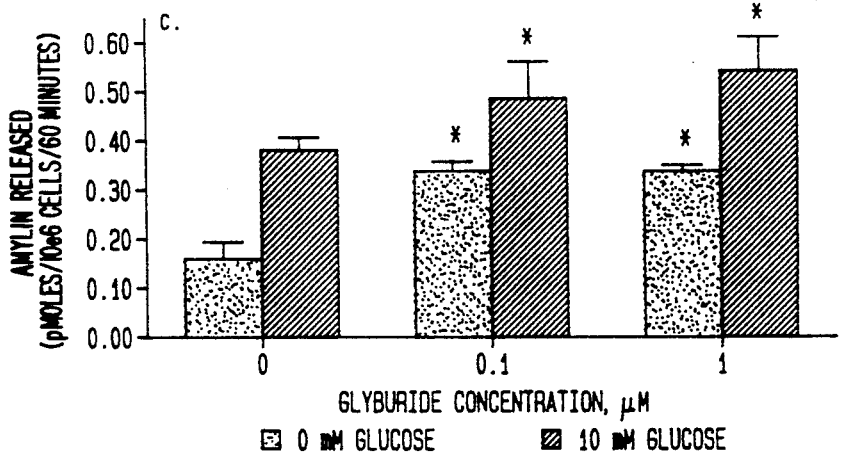

FIG. 4 shows three separate experiments in which the effects of metformin, tolbutamide, and glibenclamide on amylin secretion were examined. In each experiment it is shown that in control conditions, 10 mM glucose increased the secretion of amylin by 2.5 to 4-fold. These results indicate that HIT cells secrete amylin and increase the secretion in response to glucose as has been shown for the isolated effused pancreas (Ogawa, et al. 1990 J. Clin. Invest. 85:973-976.) FIGS. 4b and 4c show that the sulfonylurea compounds, tolbutamide and glibenclamide, significantly increase both basal and glucose-stimulated amylin secretion, at those same concentrations that, in FIG. 3, they are seen to stimulate insulin secretion. The proportional increase in amylin secretion is greater in basal conditions, approximately two-fold with glibenclamide. Thus, sulfonylurea compounds, which produce their main therapeutic effect by increasing plasma insulin levels are now demonstrated to increase the secretion of amylin, a hyperglycemic hormone that causes insulin resistance.

EXAMPLE 8

HIT T-15 cells (HIT cells; American Type Tissue Collection, Rockville, Md.) were subcultured weekly in Ham's F-12 medium (Irvine Scientific, Santa Ana, Calif.) containing 10% horse serum (Gemini Bioproducts, Calabasas, Calif.), 2.5% fetal bovine serum (FBS; Gemini), 2 mM L-glutamine, $10^5$ IU penicillin G/1, 100 mg streptomycin/1 and 10.0 mM glucose. Cells were maintained at 37° C. and 5% $CO_2$/ 95% humidified air and medium was replaced every 2 to 3 days. All experiments were performed with cells from passages 62 to 71.

Five days before each secretion study, cells were subcultured at $0.26 \times 10^6$ cells per 0.8 ml medium per well in 24-well tissue culture plates. Medium was replaced on day 3. On day 5 cells were washed twice with 1.0 plates. Medium was replaced on day 3. On day 5 cells were washed twice with 1.0 ml Krebs-Ringer buffer (KRB) containing 119 mM NaCl, 4.74 mM KCl, 2.54 mM $CaCl_2$, 1.19 mM $KH_2PO_4$, 25 mM $NaHCO_3$, 10 mM HEPES and 0.1% protease-free bovine serum albumin (Cohn fraction V; Sigma Chemical Co., St. Louis Mo.) at pH 7.4. After washing 1.0 ml KRB was added and plates were incubated for 30 minutes at 37° C. in equilibrium with air. Cells were washed twice more prior to addition of 0.5 ml KRB containing the indicated concentrations of glucose, arginine, somatostatin or glucagon (Sigma). Glucagon stock solutions contained 300 TIU aprotinin/1 (affinity purified, Sigma). After a 60 minute incubation with test substance, supernatants were centrifuged to remove cell debris, then stored at $-20°$ C. Supernatants were analyzed for insulin and amylin content by radioimmunoassay within one week of collection. Three wells per plate were trypsinized and cells per well were quantitated using a Coulter Counter (Model Zf, Coulter Electronics, Hialeah, Fla.). Data are expressed as the percentage change in pmoles of hormone released/$10^6$ cells, relative to controls (absence of test substance) or as the moles of amylin released/mole of insulin/$10^6$ cells/hour (A/I ratio).

Immunoreactive insulin content in supernatants was measured using a commercial radioimmunoassay (IM.78; Amersham, Arlington Heights, Ill.). Human insulin standards were prepared in KRB. Hamster insulin in supernatant codiluted with human standards in the range 0.50 to 1.70 pmoles/ml. The radioimmunoassay for immunoreactive amylin was as described in Example 7 above.

Figure 5:
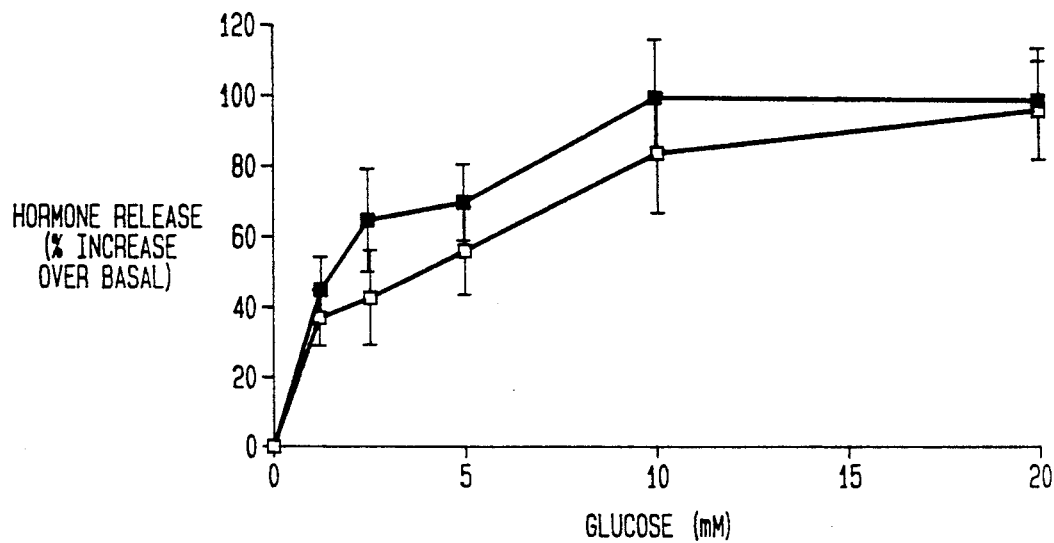
FIG. 5 shows glucose-stimulated amylin and insulin secretion from HIT cells in a dose-dependent fashion. Data are expressed as percent of basal amylin (solid square) or insulin (open square) release, which occurred in the absence of glucose. Mean±SEM of four replicate experiments. Mean basal amylin and insulin release were $0.120\pm0.026$ and $0.443\pm0.175$ pmoles/$10^6$ cells, respectively.

The amylin radioimmunoassay had a sensitivity of 8 pg amylin/ml and linear range of 200 to 800 pg/ml. Intra- and interassay coefficients of variation were 5% and 9% respectively. Hamster amylin codiluted with human amylin in the linear range. Recovery of increasing amounts of human amylin added to HIT cell supernatants was $100 \pm 15\%$ within this range. Glucagon (5 $\mu$M) and somatostatin (100 nM) had no effect on the hamster amylin displacement curve. As shown in FIG. 5, glucose stimulated amylin and insulin secretion from HIT cells in a dose-dependent manner. The half-maximal response ($EC_{50}$) for both hormones was approximately 2 mM glucose. Maximum secretion occurred at 20 mM glucose. There was a strong correlation between changes in amylin and insulin secretion in response to increasing glucose (r=0.952, p<0.0001). The mean A/I ratio was $0.44 \pm 0.02$ over the arginine concentration range tested.

Figure 6:
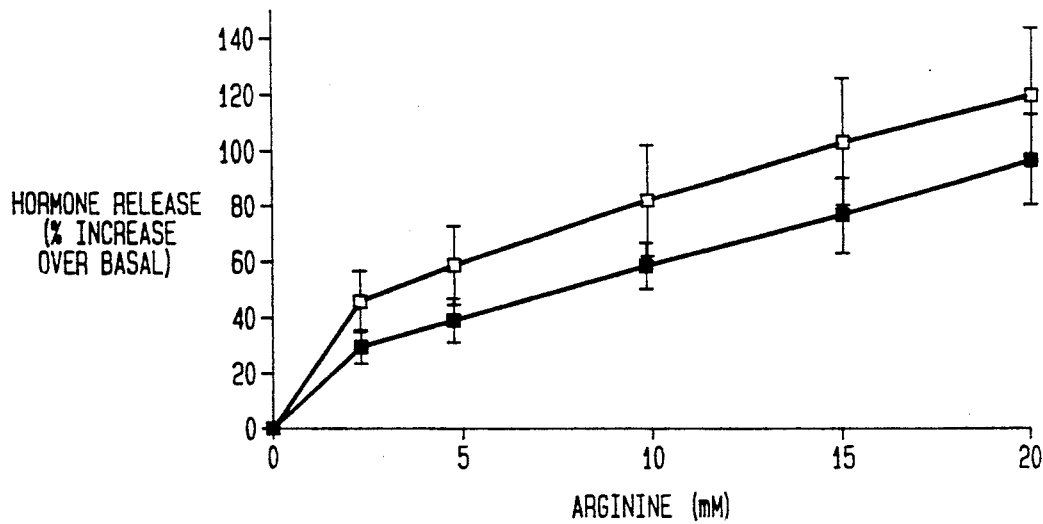
FIG. 6 shows arginine-stimulated amylin and insulin secretion from HIT cells in a dose-dependent manner. HIT cells were incubated for 60 minutes with increasing concentrations of arginine. Data are expressed as percent of basal amylin (solid square) or insulin (open square) release, which occurred in the absence of arginine. Mean±SEM of seven replicate experiments. Mean basal amylin and insulin release were $0.145\pm0.035$ and $0.369\pm0.073$ pmoles/$10^6$ cells, respectively.
Figure 7:
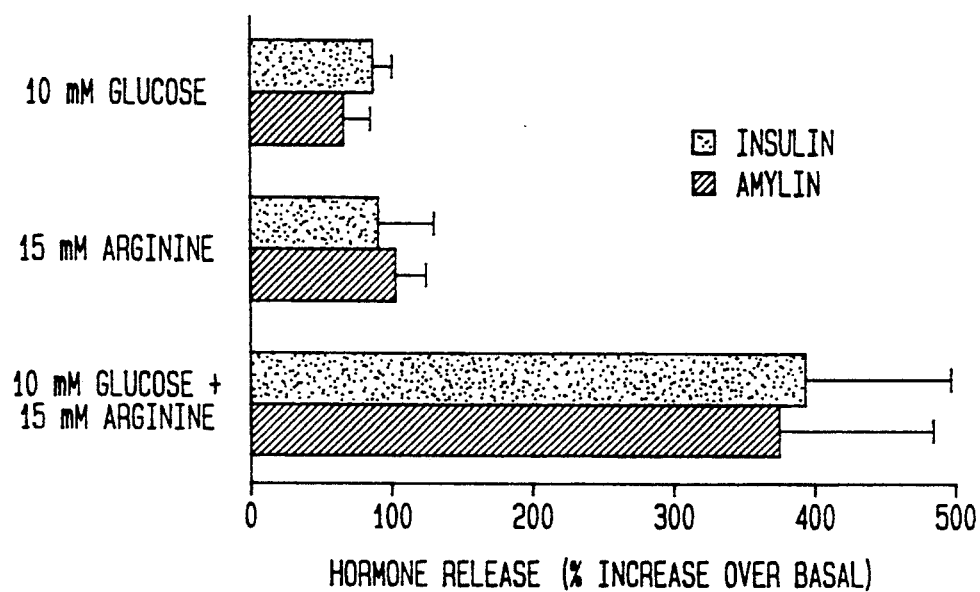
FIG. 7 shows the arginine enhancement of glucose-stimulated amylin and insulin secretion from HIT cells. HIT cells were incubated for 60 minutes with glucose or arginine alone or in combination. Data are expressed as percent of basal amylin or insulin release (absence of secretagogues). Mean±SEM of three replicate experiments. Mean basal amylin and insulin release were $0.184\pm0.047$ and $0.489\pm0.070$ pmoles/$10^6$ cells, respectively.

Arginine also stimulated amylin and insulin secretion in a dose-dependent manner (FIG. 6). A maximum secretory response was not observed under these conditions. The trends in amylin and insulin secretion in response to increasing arginine were identical (r=0.926, p<0.0001). The mean A/I ratio was $0.44 \pm 0.02$ over the arginine concentration rang tested. Arginine has been shown to potentiate glucose-stimulated secretion from isolated, perfused rat pancreata. In addition, this potent secretagogue combination increased the A/I ratio relative to glucose or arginine alone. To determine if glucose plus arginine could uncouple the secretion of amylin and insulin from HIT cells, the secretory response to 10 mM glucose or 15 mM arginine alone or in combination was evaluated (FIG. 7). The secretory response to combined secretagogue exceeded the sums of the individual responses for both amylin and insulin. However, the A/I ratio did not increase with the more potent combination of glucose and arginine relative to either secretagogue alone (glucose: $0.32 \pm 0.01$; arginine: $0.41 \pm 0.05$; glucose plus arginine: $0.34 \pm 0.01$; n=3).

Figure 8:
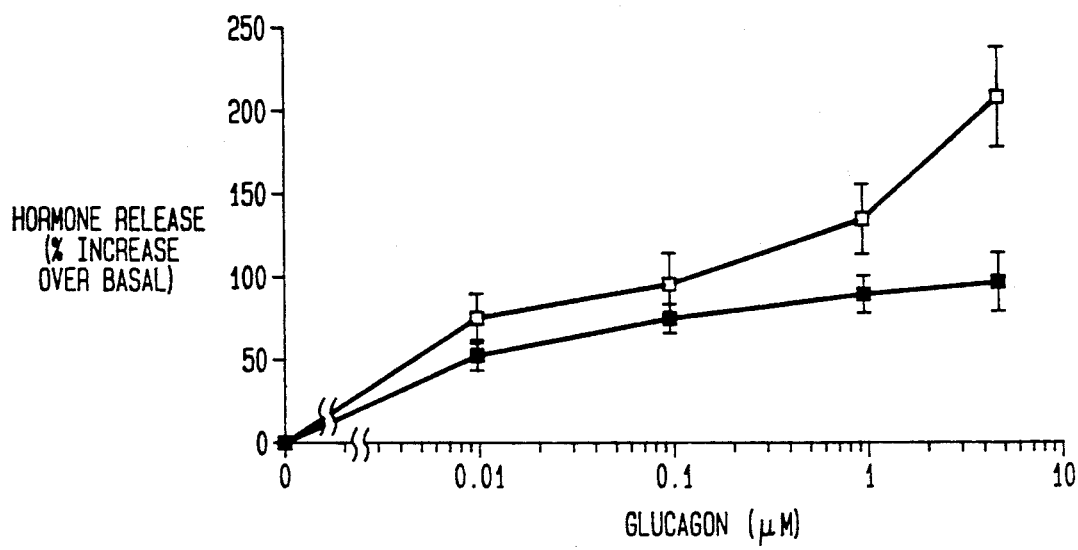
FIG. 8 shows the glucagon enhancement of amylin and insulin release from HIT cells primed with glucose and arginine. Data are expressed as percent of amylin (solid square) or insulin (open square) released in the absence of glycogen. Mean ±SEM of four replicate experiments. Mean amylin and insulin release in control wells (1.25 mM glucose plus 1.25 mM arginine) were $0.367\pm0.096$ and $1.058\pm0.316$ pmoles/$10^6$ cells, respectively.
Figure 9:
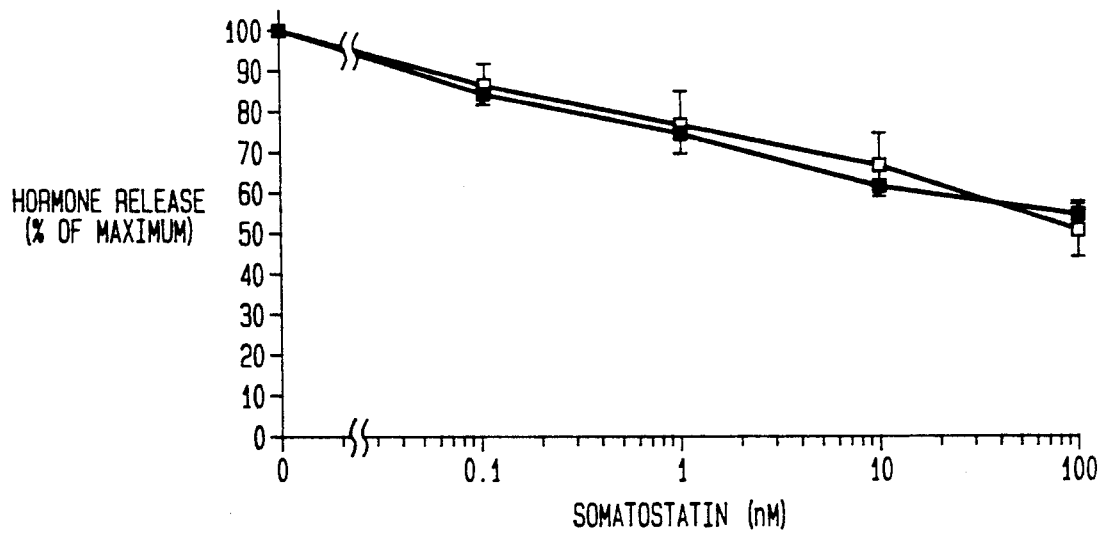
FIG. 9 shows the somatostatin suppression of amylin and insulin release from HIT cells challenged with glucose and arginine. Data are expressed as percent of maximum amylin (solid square) or insulin (open square) release, which occurred in the absence of somatostatin. Mean ±SEM of three replicate experiments. Mean amylin and insulin release in control wells (10 mM glucose plus 15 mM arginine) were $0.528\pm0.254$ and $1.617\pm0.877$ pmoles/$10^6$ cells, respectively.

Glucagon and somatostatin modulation of amylin and insulin release are illustrated in FIGS. 8 and 9. As shown in FIG. 8, glucagon enhanced both amylin and insulin release from HIT cells primed with 1.25 mM glucose plus 1.25 mM arginine. Enhancement was dosedependent, however glucagon-induced greater secretion rates resulted in a modest decrease in the A/I ratio with increasing glucagon (Table 6).

Somatostatin suppressed both amylin and insulin release from HIT cells challenged with 10 mM glucose plus 15 mM arginine (FIG. 9). Decreases in amylin and insulin secretion were proportional with increasing somatostatin (r=0.001, p<0.0001) and the A/I ratio remained constant at $0.36 \pm 0.02$ over the somatostatin concentration range tested.

TABLE 6

Effects of increasing glucagon concentrations on mean A/I secretion ratio.

| Glucagon Concentration ($\mu M$) | n | A/I Ratio |
| --- | --- | --- |
| 0.0 | 14 | 0.39 ± 0.08 |
| 0.01 | 15 | 0.34 ± 0.11 |
| 0.1 | 15 | 0.35 ± 0.13 |
| 1.0 | 15 | 0.35 ± 0.09 |
| 5.0 | 16 | 0.26 ± 0.08+ |

A/I ratio (mean ± SD) determined for n individual wells. Data are taken from experiments described in FIG. 5. + denotes significant difference from controls (absence of glucagon); ANOVA, Dunnett's test; $p < 0.05$.

We claim:

1. A method for the treatment of non-insulin dependent, or type 2, diabetes mellitus in a patient, which comprises the administration to said patient of a hypoglycemic agent that enhances plasma concentrations of amylin, said hypoglycemic agent being administered in conjunction with a therapeutically effective amount of an amylin antagonist.

2. The method of claim 1 wherein said hypoglycemic agent that enhances plasma concentrations of amylin is a sulfonylurea hypoglycemic agent.

3. The method of claim 2 wherein said sulfonylurea hypoglycemic agents also enhances plasma concentrations of insulin.

4. The method of claim 2 wherein said sulfonylurea hypoglycemic agent is glibenclamide.

5. The method of claim 2 wherein said sulfonylurea is tolbutamide.

6. A method for enhancing the blood glucose lowering effects of a hypoglycemic agent that is useful in the treatment of hyperglycemia and which, when administered for said treatment, results in increased levels of circulating amylin, comprising the administration of a therapeutically effective amount of an amylin antagonist in conjunction with said hypoglycemic agent.

7. The method of any of claims 1-5 or 6 wherein said hypoglycemic agents and said amylin antagonist are administered together.

8. The method of any of claims 1-5 or 6 wherein said hypoglycemic agent and said amylin antagonist are not administered together.

9. A composition comprising, in a pharmaceutically acceptable carrier, therapeutically effective amounts of a hypoglycemic agent that enhances plasma concentrations of amylin and an amylin antagonist.

10. The composition of claim 9 wherein said hypoglycemic agent that enhances plasma concentrations of amylin is a sulfonylurea hypoglycemic agent.

11. The composition of claim 9 wherein said hypoglycemic agent that enhances plasma concentrations of amylin also enhances plasma concentrations of insulin.

12. The composition of claim 10 wherein said sulfonylurea hypoglycemic agent is glibenclaminde.

13. The composition of claim 10 wherein said sulfonylurea hypoglycemic agent is tolbutamide.

* * * * *